(12) United States Patent
Gualtieri et al.

(10) Patent No.: US 11,515,033 B2
(45) Date of Patent: Nov. 29, 2022

(54) AUGMENTED INSPECTOR INTERFACE WITH TARGETED, CONTEXT-DRIVEN ALGORITHMS

(71) Applicant: GE Precision Healthcare LLC, Milwaukee, WI (US)

(72) Inventors: James Gualtieri, Pittsburgh, PA (US); Axel Crasemann, Wilmette, IL (US)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 213 days.

(21) Appl. No.: 16/855,635

(22) Filed: Apr. 22, 2020

(65) Prior Publication Data
US 2021/0335481 A1 Oct. 28, 2021

(51) Int. Cl.
*G16H 30/40* (2018.01)
*G06F 3/0482* (2013.01)
*G06T 7/00* (2017.01)

(52) U.S. Cl.
CPC ........... *G16H 30/40* (2018.01); *G06F 3/0482* (2013.01); *G06T 7/0012* (2013.01); *G06T 2207/30016* (2013.01); *G06T 2207/30064* (2013.01); *G06T 2207/30096* (2013.01)

(58) Field of Classification Search
CPC ..... G16H 30/40; G06F 3/0482; G06T 7/0012; G06T 2207/30016; G06T 2207/30064; G06T 2207/30096
See application file for complete search history.

(56) References Cited

U.S. PATENT DOCUMENTS

| | | | | |
|---|---|---|---|---|
| 2007/0294112 | A1* | 12/2007 | Settimi | G16H 10/60 705/3 |
| 2018/0157928 | A1* | 6/2018 | Oliveira | G16H 30/40 |
| 2019/0365235 | A1* | 12/2019 | Di Tullio | A61B 5/441 |

FOREIGN PATENT DOCUMENTS

| | | | | |
|---|---|---|---|---|
| EP | 2977922 A2 * | 1/2016 | | G06T 7/0012 |
| EP | 3477655 A1 * | 5/2019 | | A61B 5/0013 |
| WO | WO-2019210292 A1 * | 10/2019 | | A61B 8/0825 |

* cited by examiner

*Primary Examiner* — Xin Sheng
(74) *Attorney, Agent, or Firm* — Amin, Turocy & Watson, LLP

(57) ABSTRACT

Systems and techniques that facilitate an augmented inspector interface with targeted, context-driven algorithms are provided. In various embodiments, a magnification component can magnify a portion of a medical image. In various embodiments, a recognition component can recognize an anatomical structure depicted in the portion of the medical image. In various embodiments, a recommendation component can recommend one or more sets of computing algorithms or computing operations related to the anatomical structure. In various embodiments, a menu component can display the one or more recommended sets of computing algorithms or computing operations in a drop-down menu.

20 Claims, 16 Drawing Sheets

AUGMENTED INSPECTOR INTERFACE WITH TARGETED, CONTEXT-DRIVEN ALGORITHMS

TECHNICAL FIELD

The subject disclosure relates generally to user interfaces, and more specifically to augmented inspector interfaces that employ artificial intelligence to recommend and spatially target/localize computing algorithms and/or computing operations related to a context of a medical image.

BACKGROUND

Conventional computing user interfaces for analyzing, evaluating, and/or inspecting medical images provide only standard image analysis, evaluation, and/or inspection tools (e.g., magnifying glass). Moreover, such conventional computing user interfaces provide the same image analysis, evaluation, and/or inspection tools across all medical images. Furthermore, existing artificial intelligence algorithms for analyzing, evaluating, and/or inspecting medical images generally must be run in preprocessing modes, often take minutes to run on large study-level data sets, and each have their own disjoint viewer, interface, and/or mini-application. An improved computing user interface for analyzing, evaluating, and/or inspecting medical images that can address one or more of these problems is therefore desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate augmented inspector interfaces with targeted, context-driven algorithms are described.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise a magnification component. In various aspects, the magnification component can magnify a portion of a medical image. In various embodiments, the computer-executable components can further comprise a recognition component. In various instances, the recognition component can recognize an anatomical structure depicted in the portion of the medical image. In various embodiments, the computer-executable components can further comprise a recommendation component. In various cases, the recommendation component can recommend one or more sets of computing algorithms or computing operations based on the recognized anatomical structure. In various embodiments, the computer-executable components can further comprise a menu component. In various aspects, the menu component can display the one or more recommended sets of computing algorithms or computing operations in a drop-down menu.

According to one or more embodiments, the above-described system can be implemented as a computer-implemented method and/or a computer program product.

DETAILED DESCRIPTION

Figure 1:
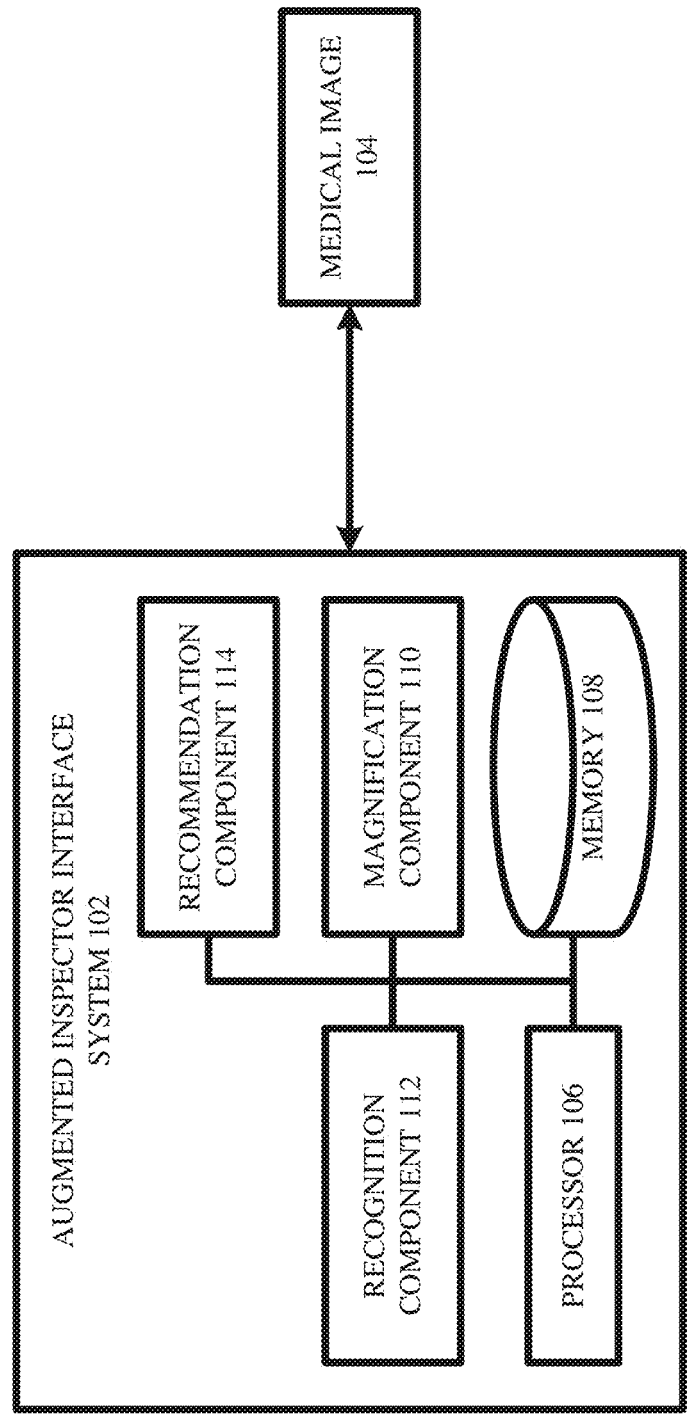
FIG. 1 illustrates a block diagram of an example, non-limiting system that facilitates an augmented inspector interface with targeted, context-driven algorithms in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Modern medical diagnostic techniques rely heavily on the analysis, evaluation, and/or inspection of medical images (e.g., X-ray images, computed tomography (CT) images, magnetic resonance imaging (MRI) images, ultrasound images, positron emission tomography (PET) images, and/or any other suitable medical images). To aid in this analysis, evaluation, and/or inspection, computerized user interfaces exist that allow clinicians, researchers, and/or other health care providers/professionals to apply various computerized analysis, evaluation, and/or inspection tools to a medical image (e.g., a computerized user interface can display a computerized, movable magnifying glass tool that magnifies on a display screen the portion of the medical image over which the movable magnifying glass tool is placed). Such computerized user interfaces typically provide only standard analysis, evaluation, and/or inspection tools (e.g., magnifying glass) and require the clinician, researcher, and/or other health care provider/professional to manually analyze, evaluate, and/or inspect the medical image. Moreover, such computerized user interfaces provide the same analysis, evaluation, and/or inspection tools across all medical images, regardless of the specific/particular context of the current medical image being analyzed, evaluated, and/or inspected. Furthermore, many artificial intelligence algorithms that are useful for analyzing, evaluating, and/or inspecting medical images run in their own viewer, interface, and/or mini-application and are not offered in a single, unified user interface. Further still, such artificial intelligence algorithms often take minutes to run and must be implemented in a pre-processing mode because of the large input size of medical image files.

Various embodiments of the subject innovation can address one or more of these issues/problems. One or more embodiments described herein include systems, computer-implemented methods, apparatus, and/or computer program products that can facilitate an augmented inspector interface with targeted, context-driven algorithms. In various instances, embodiments of the subject innovation can be considered a computerized magnifying glass tool for analysis, evaluation, and/or inspection of medical images that exhibits enhanced functionality as described herein. Such enhanced functionality can simplify work processes confronted by health care professionals (e.g., radiologists) and can improve the accuracy and/or efficiency of analyses, evaluations, and/or inspections of medical images, which can correspondingly improve the efficacy of resulting medical diagnoses.

Specifically, in various instances, embodiments of the subject innovation can magnify, via a magnification component, a portion of a medical image (e.g., can magnify a portion of an X-ray scan, a portion of a CT scan, a portion of an MRI scan, a portion of a PET scan, a portion of an ultrasound scan). In various aspects, the magnification component can generate and display on a computer screen/monitor a computerized magnifying glass tool that is movable and/or placeable over the electronically/digitally displayed medical image by a clinician and that magnifies the portion of the medical image over which the computerized magnifying glass tool is moved and/or placed. In various cases, the clinician can move and/or place the computerized magnifying glass tool by interacting with a computer mouse and/or any other suitable human-computer interface device (e.g., touch screen, joystick, keyboard, keypad, motion capture).

In various instances, embodiments of the invention can recognize, via a recognition component, an anatomical structure depicted in the magnified portion of the medical image. In various instances, the anatomical structure can be any suitable anatomical structure at any suitable level of granularity and/or detail (e.g., tumor, nodule, blood vessel, artery, lung, chest, ribcage, heart, atrium, ventricle, femur, quadricep, spine, spinal cord, brain, cerebral cortex, eye, cornea, abdomen, small intestine, white blood cells, and so on). In various aspects, the recognition component can employ a machine learning classifier that is trained to recognize and classify/label the anatomical structure that is depicted in the magnified portion of the medical image. In various instances, the machine learning classifier can be trained to receive as input the magnified portion of the medical image and produce as output a classification/label that identifies and/or infers the anatomical structure depicted in the magnified portion of the medical image (e.g., the machine learning classifier can recognize the context of the medical image based on image recognition and/or computer vision). In various instances, the machine learning classifier can be trained to receive as input metadata pertaining to the medical image (e.g., Digital Imaging and Communications in Medicine (DICOM) standard metadata) and produce as output a classification/label that identifies and/or infers the anatomical structure depicted in the magnified portion of the medical image (e.g., the machine learning classifier can recognize the context of the medical image based on the metadata related to the medical image). In various aspects, the machine learning classifier can be trained via supervised learning, unsupervised learning, reinforcement learning, and/or any other suitable training scheme.

In various instances, embodiments of the subject innovation can recommend, via a recommendation component, one or more sets of computing algorithms and/or computing operations that are related to the recognized anatomical structure (e.g., if the recognition component infers that the anatomical structure is a lymph node, the recommendation component can recommend that lymph-node-specific computing algorithms/operations be applied to the magnified portion of the medical image; if the recognition component infers that the anatomical structure is a kidney, the recommendation component can recommend that kidney-specific computing algorithms/operations be applied to the magnified portion of the medical image). In various aspects, the recommendation component can leverage an ontology that maps anatomical structures to related and/or relevant computing algorithms and/or computing operations. In various aspects, the recommendation component can recommend one or more sets of computing algorithms and/or computing operations that are related to the anatomical structure, based on increasing and/or decreasing generality. For example, if the recognition component infers that the anatomical structure is a lung nodule depicted in a CT scan, the recommendation component can recommend a set of nodule-centric algorithms (e.g., most specific level of granularity), a set of lung-centric algorithms (e.g., less specific/granular than nodule-centric algorithms), a set of chest-centric algorithms (e.g., less specific/granular than lung-centric algorithms), a set of CT-centric algorithms (e.g., less specific/granular than chest-centric algorithms), and/or a set of generic, remaining, and/or other medical image analysis algorithms (e.g., most general level of granularity). In various instances, any suitable computing algorithms/operations can be implemented, and various embodiments of the subject innovation can recommend relevant ones of those computing algorithms/operations to a clinician, based on one or more recognized anatomical structures depicted in the medical image.

In various instances, embodiments of the subject innovation can display, via a menu component, the recommended sets of computing algorithms and/or computing operations in a drop-down menu (e.g., a drop-down menu that is displayed on the computer screen/monitor as adjacent to the magnified portion of the medical image and/or adjacent to the computerized magnifying glass tool). In various cases, the one or more sets of recommended computing algorithms and/or computing operations can be listed in the drop-down menu in order of specificity (e.g., from most specific to most general, and/or from most general to most specific). To continue the above example where the recognition component infers that the anatomical structure is a lung nodule depicted in a CT scan, the drop-down menu can list the recommended nodule-centric algorithms near a beginning of the menu, can list the recommended lung-centric algorithms after the nodule-centric algorithms, can list the recommended chest-centric algorithms after the lung-centric algorithms, can list the recommended CT-centric algorithms after the chest-centric algorithms, and/or can list the recommended generic, remaining, and/or other medical image analysis algorithms after the CT-centric algorithms.

In various aspects, embodiments of the subject innovation can execute, via an execution component, a computing algorithm and/or computing operation selected from the one or more recommended sets of computing algorithms and/or computing operations. In various aspects, a clinician that is interacting with the subject innovation can select (e.g., via a computer mouse and/or any other suitable human-computer interface device) the selected computing algorithm and/or computing operation from the drop-down menu. In various instances, the selected computing algorithm and/or computing operation can computationally operate on the magnified portion of the medical image and can computationally ignore a remainder and/or remaining portion of the medical image (e.g., an unmagnified portion). In other words, the selected computing algorithm and/or computing operation can run on just the magnified portion of the medical image rather than on the full medical image. Since the magnified portion of the medical image can be smaller (e.g., can contain fewer pixels and/or voxels) than the full medical image, the selected computing algorithm and/or computing operation can run more quickly on the magnified portion of the medical image than it could run on the full medical image. In other words, the selected computing algorithm and/or computing operation can be targeted and/or spatially localized to the magnified portion of the medical image. In this way, real-time and/or near real-time results can be obtained because the selected computing algorithm and/or computing operation is executing on a smaller data volume (e.g., compute power required by the selected computing algorithm and/or computing operation can be reduced through spatial targeting and/or localization).

Overall, in various aspects, embodiments of the subject innovation can be implemented as a computerized user interface that can be used by a clinician (e.g., radiologist) to analyze, evaluate, and/or inspect a medical image. In various cases, the medical image can be generated by appropriate medical imaging devices (e.g., X-ray devices, CT scanners, MRI machines) that are communicatively coupled to embodiments of the subject innovation. In various aspects, the medical image can be otherwise electronically received in any suitable way by embodiments of the subject innovation (e.g., via a wired and/or wireless electronic connection). Once the medical image is received, embodiments of the subject innovation can display the medical image on a display screen (e.g., computer monitor) such that the medical image is viewable by a clinician that desires to analyze, evaluate, and/or inspect the medical image. In various aspects, embodiments of the subject innovation can generate, via the magnification component, a computerized, movable magnifying glass tool superimposed over the medical image and with which the clinician can interact (e.g., via a computer mouse and/or any other suitable human-computer interface device). In various instances, the clinician can drag and/or move the computerized, movable magnifying glass tool over any desired portion of the medical image, and the computerized, movable magnifying glass tool can magnify the portion of the medical image over which it is currently located/placed. Such magnification can assist the clinician in manually analyzing, evaluating, and/or inspecting the medical image.

As explained herein, the computerized, movable magnifying glass tool of various embodiments of the subject innovation can exhibit enhanced functionality in addition to magnifying a portion of the medical image. Specifically, in various instances, embodiments of the subject innovation can recognize a context of the medical image and recommend relevant computing algorithms/operations based on the recognized context. In other words, embodiments of the subject innovation can provide context-driven recommendations to the clinician as to which computing algorithms/operations should be executed on the medical image. Such computing algorithms/operations can, in various instances, include feature tracking algorithms, disease/infirmity recognition algorithms, and/or any other suitable computational algorithms/operations that can receive as input the magnified portion of the medical image and produce as output some medically significant result. In various aspects, embodiments of the subject innovation can recognize, via the recognition component, an anatomical structure depicted in the magnified portion of the medical image. In various aspects, the recognition component can employ a machine learning classifier that classifies/labels an anatomical structure illustrated in the medical image. In various cases, the machine learning classifier can be trained to receive as input the medical image and to produce as output the classification/label (e.g., the machine learning classifier can recognize the context of the medical image based on image recognition and/or computer vision). In various cases, the machine learning classifier can be trained to receive as input metadata pertaining to the medical image (e.g., DICOM metadata) and to produce as output the classification/label (e.g., the machine learning classifier can recognize the context of the medical image based on available metadata concerning the medical image). In various instances, embodiments of the subject innovation can recommend, via the recommendation component, one or more sets of computing algorithms/operations that relate and/or are relevant to the classified/labeled anatomical structure (e.g., the recommendation component can recommend relevant computing algorithms/operations to execute on the medical image based on the recognized context of the medical image). In various aspects, the recommendation component can leverage an ontology that maps anatomical structures (e.g., body parts) to computing algorithms/operations (e.g., maps lung nodules to nodule-specific algorithms, lung-specific algorithms, and/or chest-specific algorithms; maps frontal cortex lesions to lesion-specific algorithms, frontal cortex-specific algorithms, brain-specific algorithms, and/or head-specific algorithms). In various instances, embodiments of the subject innovation can display, by the menu component, a drop-down menu that contains/lists the one or more sets of recommended computing algorithms/operations. In various cases, the drop-down menu can list the one or more recommended sets of computing algorithms/operations in order of specificity/generality, and the drop-down menu can be displayed as adjacent to the computerized, movable magnifying glass tool.

Thus, in various aspects, embodiments of the subject innovation can provide a computerized user interface that can assist a clinician in analyzing, evaluating, and/or inspecting a medical image by automatically recognizing a context of the medical image (e.g., recognizing an anatomical structure depicted in the magnified portion of the medical image) and automatically recommending/suggesting a list of computing algorithms and/or computing operations to execute on the medical image based on the recognized context. As explained above, embodiments of the subject innovation can provide a computerized, movable magnifying glass tool that is selectable and/or controllable by the clinician to magnify a desired portion of the medical image. Moreover, the computerized, movable magnifying glass tool can recognize an anatomical structure depicted in the magnified portion of the medical image and can recommend one or more relevant computing algorithms/operations that can and/or should be executed on the magnified portion of the medical image. In other words, embodiments of the subject innovation can automatically suggest/recommend applicable and/or relevant computational algorithms/operations based on the context of the medical image (e.g., based on the depicted/illustrated anatomical structure). For example, if a lung lymph node is detected in the magnified portion of the medical image, relevant computing algorithms/operations can be recommended (e.g., lymph node algorithm, lung algorithm, chest algorithm) so that the clinician does not waste time wading through irrelevant computing algorithms/operations (e.g., brain algorithm, head algorithm, spinal cord algorithm, kidney algorithm). Because embodiments of the computerized, movable magnifying glass tool described herein can automatically recognize pictured anatomical structures and recommend relevant computing algorithms/operations, such embodiments constitute concrete technical improvements in the field of medical/diagnostic user interfaces.

Furthermore, in various aspects, embodiments of the subject innovation can execute, via the execution component, a computing algorithm/operation selected from the one or more recommended sets of computing algorithms/operations. In various cases, the clinician can select (e.g., via the computer mouse) a desired computing algorithm/operation from the drop-down menu. In various instances, the execution component can cause the selected computing algorithm/operation to execute (e.g., to computationally operate) on the magnified portion of the medical image and to not execute (e.g., to computationally ignore) the remainder of the medical image. In this way, a size of input data fed to the selected computing algorithm/operation can be decreased, which can correspondingly decrease compute power and compute time required by the selected computing algorithm/operation. In other words, embodiments of the computerized, movable magnifying glass tool disclosed herein can spatially target and/or localize application of computing algorithms/operations, which can correspondingly speed up the time it takes to analyze and/or evaluate the medical image.

Overall, embodiments of the subject innovation can provide a user interface (e.g., a computerized, movable magnifying glass tool) that exhibits improved/enhanced functionality (e.g., can automatically recognize a magnified anatomical structure depicted in a medical image, can automatically recommend relevant diagnostic algorithms/operations for analyzing the recognized anatomical structure, and can spatially localize/target a selected diagnostic algorithm/operation to speed up analysis of the medical image). In this way, embodiments of the subject innovation can offer targeted, context-driven computing algorithms to clinicians, which can assist a clinician in more accurately and more quickly analyzing, evaluating, and/or inspecting medical images of patients. Thus, embodiments of the subject innovation constitute concrete, technical improvements in the field of medical/diagnostic user interfaces.

Various embodiments of the subject innovation can be employed to use hardware and/or software to solve problems that are highly technical in nature (e.g., to facilitate augmented inspector interfaces with spatially targeted/localized, context-driven algorithms), that are not abstract and that cannot be performed as a set of mental acts by a human. Further, some of the processes performed can be performed by a specialized computer (e.g., trained machine learning classifier) for carrying out defined tasks related to computerized user interfaces for analyzing, evaluating, and/or inspecting medical images (e.g., magnifying a portion of a medical image, recognizing an anatomical structure depicted in the portion of the medical image, recommending computing algorithms/operations relevant to the recognized anatomical structure, displaying the recommended computing algorithms/operations in a drop-down menu, executing a selected computing algorithm/operation on the portion of the medical image and not on the remainder of the medical image to speed up analysis). Such defined tasks are not conventionally performed manually by humans. Moreover, neither the human mind nor a human with pen and paper can display in a drop-down menu recommended computing algorithms/operations or execute a selected one of those computing algorithms/operations in a spatially targeted/localized manner. Instead, various embodiments of the subject innovation are inherently and inextricably tied to computer technology and cannot be implemented outside of a computing environment (e.g., embodiments of the subject innovation constitute an enhanced user interface that facilitates targeted and context-driven analysis of medical images; such a user interface can exist only in a computing environment). In various instances, embodiments of the invention can integrate into a practical application the disclosed teachings regarding user interfaces that facilitate targeted, context-driven analysis of medical images. Indeed, in various embodiments, the disclosed teachings can provide a computerized, movable magnifying glass tool with enhanced functionality (e.g., rather than merely magnifying portions of a medical image, the disclosed embodiments can automatically recognize an anatomical structure depicted in the magnified portion of the medical image, can automatically recommend from a collection of available computing algorithms/operations those computing algorithms/operations that are related to the recognized/identified anatomical structure, and/or can facilitate spatial localization/targeting of a selected computing algorithm/operation by executing it only on the magnified portion of the medical image and not on the whole medical image). Such an improved user interface can result in quicker and more accurate analysis, evaluation, and/or inspection of medical images by clinicians, and so such an improved user interface is clearly a useful and practical application of computers.

Moreover, various embodiments of the invention can provide technical improvements to and solve problems that arise in the field of medical/diagnostic user interfaces. After all, existing medical/diagnostic user interfaces simply do not automatically recognize an anatomical structure depicted in a computerized magnifying glass tool or automatically recommend computing algorithms/operations relevant to the recognized anatomical structure to execute on the magnified portion of the image. Furthermore, existing medical/diagnostic user interfaces do not spatially localize/target selected computing algorithms/operations such that the selected algorithm/operation computationally operates only on the magnified portion of the medical image and computationally ignores (e.g., does not operate on) the remaining, unmagnified portion of the medical image. Thus, embodiments of the subject innovation provide enhanced capabilities/functions that are not performed by conventional medical/diagnostic user interfaces.

Furthermore, various embodiments of the subject innovation can control real-world devices based on the disclosed teachings. For example, embodiments of the subject innovation can electronically receive a real-world medical image (e.g., X-ray scan, CT scan, MRI scan, PET scan, ultrasound scan), can display the medical image on a real-world display screen (e.g., computer monitor), and can also display on the real-world display screen and over top of the medical image a computerized, movable magnifying glass tool with which a real-world clinician can interact (e.g., via a real-world computer mouse and/or any other suitable interface device). Specifically, the clinician can place the displayed, computerized, movable magnifying glass tool over a desired portion of the medical image, and the computerized, movable magnifying glass tool can magnify that portion of the medical image (e.g., to help facilitate manual analysis, evaluation, and/or inspection of the medical image by the clinician). Moreover, the computerized, movable magnifying glass tool can automatically recognize (e.g., via any suitable trained machine learning classifier) a real-world anatomical structure depicted in the magnified portion of the medical image and can automatically recommend one or more sets of real-world computing algorithms/operations that are related to the recognized anatomical structure (e.g., can automatically suggest one or more potentially useful algorithms/operations that can and/or should be executed on the magnified portion of the medical image to yield medically significant results). The computerized, movable magnifying glass tool can display on the real-world display screen these recommended algorithms/operations in a real-world drop-down menu with which the real-world clinician can interact. Further still, once the clinician selects (e.g., via the computer mouse) a desired one of the recommended algorithms/operations, the computerized, movable magnifying glass tool can execute the selected algorithm/operation on the magnified portion of the medical image in a spatially targeted/localized manner (e.g., such that the selected algorithm/operation does not execute on the unmagnified portion of the medical image). Such embodiments provide for enhanced/improved user interfaces that assist clinicians in analyzing, evaluating, and/or inspecting medical images, and thus constitute a concrete and tangible technical improvement in the field of medical/diagnostic user interfaces.

FIG. 1 illustrates a block diagram of an example, non-limiting system 100 that can facilitate an augmented inspector interface with targeted, context-driven algorithms in accordance with one or more embodiments described herein. As shown, an augmented inspector interface system 102 can, in various instances, assist in the analysis, evaluation, and/or inspection of a medical image 104 by a clinician (e.g., radiologist, researcher, and/or any other suitable health care provider, human or otherwise). In various embodiments, the medical image 104 can be any suitable digital and/or electronic image generated by any suitable medical imaging technique/device. For example, the medical image 104 can be an X-ray scan, can be a CT scan, can be an MRI scan, can be a PET scan, can be an ultrasound scan, can be a digital photograph taken in the visible spectrum, can be a digital photograph taken in the infrared spectrum, can be a thermal image, can be a microscope image, and/or can be any other suitable digital/electronic image generated for medical purposes. In various instances, multiple medical images 104 can be implemented. In various aspects, the medical image 104 can be electronically and/or digitally displayed on any suitable display screen (e.g., computer monitor) so that a clinician can view, analyze, evaluate, and/or inspect the medical image 104. In various cases, the medical image 104 can be associated with a patient (e.g., human, animal) and can depict, in various instances, one or more anatomical structures of the patient (e.g., one or more body parts at any suitable level of granularity and/or specificity). For example, the medical image 104, in some cases, can depict individual cells and/or groups of cells of the patient; arteries, veins, and/or blood vessels of the patient; nodules, lymph nodes, and/or tumors of the patient; skin lesions of the patient; a lung and/or portion of a lung of the patient; a brain and/or portion of a brain of the patient; a kidney and/or portion of a kidney of the patient; a skeletal structure and/or portion of a skeletal structure of the patient; muscle fibers and/or portion of muscle fibers of the patient; a nervous system structure and/or portion of a nervous system structure of the patient; a digestive system structure and/or portion of a digestive system structure of the patient; an endocrine system structure and/or a portion of an endocrine system structure of the patient; a cardiovascular system structure and/or portion of a cardiovascular system structure of the patient; a respiratory system structure and/or portion of a respiratory system structure of the patient; and/or any other suitable portion and/or sub-portion of the anatomy of the patient at any suitable level of granularity.

In various aspects, the augmented inspector interface system 102 can be communicatively coupled to the medical image 104 via any suitable wired and/or wireless electronic connection.

As explained herein, the augmented inspector interface system 102 can exhibit enhanced functionality that can assist a clinician in analyzing, evaluating, and/or inspecting the medical image 104 for diagnostic purposes. Specifically, in various embodiments, the augmented inspector interface system 102 can magnify a portion of the medical image 104, can automatically recognize an anatomical structure depicted in the magnified portion of the medical image 104, and can automatically recommend one or more computing algorithms/operations to execute on the magnified portion of the medical image 104. In various aspects, the augmented inspector interface system 102 can spatially target/localize a selected one of the recommended computing algorithms/operations to execute on the magnified portion of the medical image 104.

In various embodiments, the augmented inspector interface system 102 can comprise a processor 106 (e.g., computer processing unit, microprocessor) and a computer-readable memory 108 that is operably and/or operatively and/or communicatively connected/coupled to the processor 106. The memory 108 can store computer-executable instructions which, upon execution by the processor 106, can cause the processor 106 and/or other components of the augmented inspector interface system 102 (e.g., magnification component 110, recognition component 112, recommendation component 114) to perform one or more acts. In various embodiments, the memory 108 can store computer-executable components (e.g., magnification component 110, recognition component 112, recommendation component 114), and the processor 106 can execute the computer-executable components.

In various embodiments, the augmented inspector interface system 102 can comprise a magnification component 110. In various instances, the magnification component 110 can magnify a portion of the medical image 104. For example, the magnification component 110 can generate and/or can be implemented as a computerized, movable magnifying glass tool electronically and/or digitally displayed on the display screen (e.g., computer monitor) and superimposed over the medical image 104. In various aspects, the clinician can move and/or interact with the computerized, movable magnifying glass tool via a computer mouse and/or any other suitable human-computer interface device (e.g., touch screen, keyboard, keypad, joystick, motion capture). In various cases, the computerized, movable magnifying glass tool can magnify a portion of the medical image 104 over which the computerized, movable magnifying glass tool is placed and/or moved (e.g., the computerized, movable magnifying glass tool can display on the display screen a magnified view of the portion of the medical image 104 over which the computerized, movable magnifying glass tool is located). So, in some instances, the clinician can place the computerized, movable magnifying glass tool over a desired portion of the medical image 104 (e.g., a portion of interest), and the computerized, movable magnifying glass tool can display on the display screen a magnified view of the desired portion, thereby allowing the clinician to more easily analyze, evaluate, and/or inspect the desired portion of the medical image 104.

In various embodiments, the augmented inspector interface system 102 can comprise a recognition component 112. In various instances, the recognition component 112 can recognize an anatomical structure depicted in the magnified portion of the medical image 104. For example, the recognition component 112 can employ a machine learning classifier that can be trained to recognize, identify, and/or infer the identity of an anatomical structure illustrated in the magnified portion of the medical image 104. In various embodiments, the machine learning classifier can employ any suitable machine learning, deep learning, artificial intelligence, and/or classification/labeling paradigm (e.g., linear and/or non-linear classification techniques). In various aspects, the machine learning classifier can be trained to receive as input the magnified portion of the medical image 104 and to produce as output a classification/label that identifies an anatomical structure depicted in the magnified portion of the medical image 104 and/or that indicates that no recognizable anatomical structure is depicted in the magnified portion of the medical image 104 (e.g., the machine learning classifier can be trained to employ image recognition, pattern recognition, and/or computer vision). For instance, suppose that the magnified portion of the medical image 104 depicts a lesion in the brain of the patient. In various aspects, the trained machine learning classifier (e.g., neural network) can receive the magnified portion of the medical image 104 as input, can analyze the magnified portion of the medical image 104, and can produce as output a classification/label indicating that the magnified portion of the medical image 104 depicts a brain lesion. In various other aspects, the machine learning classifier can be trained to receive as input DICOM metadata and/or any other suitable metadata characterizing the medical image 104 and to produce as output a classification/label that identifies an anatomical structure depicted in the magnified portion of the medical image 104 (e.g., the machine learning classifier can be trained to employ metadata recognition). For example, suppose that the magnified portion of the medical image 104 depicts a tumor in the brain of a patient. In various aspects, the trained machine learning classifier can receive metadata (e.g., DICOM metadata and/or any other suitable medical metadata) regarding the medical image 104 (e.g., size of the medical image 104, dimensions of the medical image 104, bit depth of the medical image 104, modality used to create the medical image 104, equipment settings used to capture the medical image 104, hospital department that generated the medical image 104, diagnostic purpose of the medical image 104). In various cases, the metadata can indicate that the medical image 104 is a CT scan of a brain of a patient admitted to an oncology department. Thus, the machine learning classifier can, in some cases, infer that the magnified portion of the medical image 104 depicts a brain tumor of the patient. In various aspects, the recognition component 112 can employ and/or leverage any other suitable mathematical, statistical, and/or computing technique to recognize and/or infer the identity of an anatomical structure depicted in the magnified portion of the medical image 104.

In various embodiments, the augmented inspector interface system 102 can comprise a recommendation component 114. In various instances, the recommendation component 114 can recommend one or more sets of computing algorithms and/or computing operations based on the anatomical structure recognized by the recognition component 112. In various aspects, the one or more sets of computing algorithms and/or computing operations can be any suitable computational algorithm/operation that can be executed on the medical image 104 (and/or a portion thereof) in order to generate medically significant results. Non-limiting examples of computing algorithms and/or computing operations that can be executed on the medical image 104 can include feature tracking algorithms (e.g., which can be trained to search for the anatomical structure in prior medical images of the same patient to track a size of the anatomical structure over time), diagnostic algorithms (e.g., which can be trained to recognize symptoms exhibited by the anatomical structure to determine whether the anatomical structure is afflicted with a disease/ailment), prognostic algorithms (e.g., which can be trained to predict and/or forecast a temporal evolution of a disease/affliction of the anatomical structure based on the current state of the anatomical structure), treatment algorithms (e.g., which can be trained to recommend treatment for a disease/affliction of the anatomical structure based on the current state of the anatomical structure), and/or any other suitable computing algorithms/operations that can receive as input the medical image 104 (and/or a portion thereof) and generate as output a medically significant result. In various aspects, the recommendation component 114 can leverage an ontology and/or mapping that maps anatomical structures to relevant computing algorithms and/or computing operations. For example, an ontology/mapping can link blood vessels to blood-vessel-related computing algorithms/operations, can link brain lesions to brain-lesion-related computing algorithms/operations, can link lungs to lung-related computing algorithms/operations, and/or can link tumors to tumor-related algorithms/operations. In various aspects, any suitable computing algorithms/operations can be implemented, and the recommendation component 114 can recommend to the clinician, from a collection of available computing algorithms/operations, those available computing algorithms/operations that are relevant to the medical image 104 (e.g., those computing algorithms/operations that are related to the recognized anatomical structure). Thus, the clinician need not waste time or resources searching for and/or determining the identities of relevant computing algorithms/operations.

Overall, as explained herein, embodiments of the augmented inspector interface system 102 can offer enhanced inspection functionality that can assist a clinician in analyzing, evaluating, and/or inspecting the medical image 104 by automatically recognizing an anatomical structure depicted in the medical image 104 and automatically recommending/suggesting computing algorithms/operations to be executed on the medical image 104 based on the recognized anatomical structure. In various aspects, such recognition and recommendation can assist clinicians by automatically identifying for the clinician the most relevant of the available computational tools for analyzing the medical image 104. This can reduce an amount of time required to analyze, evaluate, and/or inspect the medical image 104 because the clinician need not manually wade through lists of numerous, irrelevant computing algorithms/operations. Instead, the augmented inspector interface system 102 can quickly and automatically present to the clinician the most relevant of the available computing algorithms/operations.

To help clarify the above teachings, consider the following, non-limiting example. Suppose that the medical image 104 is an MRI scan of a patient's auditory pathway. In various aspects, the MRI scan of the patient's auditory pathway can be electronically and/or digitally displayed to a clinician that desires to analyze, evaluate, examine, and/or inspect the MRI scan of the patient's auditory pathway for diagnostic purposes. In various aspects, the magnification component 110 can generate and/or be implemented as a computerized, movable magnifying glass tool that is electronically displayed to the clinician and superimposed over the MRI scan of the patient's auditory pathway. In various aspects, the clinician can position (e.g., via a computer mouse) the computerized, movable magnifying glass tool over a desired portion of the MRI scan of the patient's auditory pathway. In various cases, the computerized, movable magnifying glass tool can magnify the desired portion of the MRI scan of the patient's auditory pathway (e.g., can electronically and/or digitally display a magnified view of the portion of the MRI scan of the patient's auditory pathway over which the computerized, magnifying glass tool is placed). Suppose that the clinician places the computerized, movable magnifying glass tool over a cochlea depicted in the MRI scan of the patient's auditory pathway. Thus, the magnification component 110 (e.g., the computerized, movable magnifying glass tool) can electronically and/or digitally display a magnified view of the cochlea. In various aspects, the recognition component 112 can recognize an anatomical structure depicted in the magnified portion of the MRI scan of the patient's auditory pathway. Since the magnified portion of the MRI scan of the patient's auditory pathway can primarily depict the cochlea over which the clinician placed the computerized, movable magnifying glass tool, the recognition component 112 (e.g., via a trained machine learning classifier) can recognize, determine, and/or infer that the magnified portion of the MRI scan of the patient's auditory pathway depicts a cochlea. In various embodiments, the recommendation component 114 can recommend one or more sets of computing algorithms and/or computer operations based on the recognized anatomical structure. Since the recognition component 112 recognized that the magnified portion of the MRI scan of the patient's auditory pathway depicts a cochlea, the recommendation component 114 can recommend/suggest one or more sets of computing algorithms and/or computing operations that are related and/or relevant to medical analysis of *cochleae*. For example, the recommendation component 114 can recommend (e.g., via an ontology and/or mapping that links anatomical structures to relevant algorithms/operations) cochlea-centric algorithms (e.g., cochlea tracking algorithms, cochlea diagnostic algorithms, cochlea prognostic algorithms, cochlea treatment algorithms), auditory-pathway-centric algorithms, ear-centric algorithms, head-centric algorithms, MRI-centric algorithms, and/or any other relevant and/or related algorithms that can analyze the MRI scan of the patient's auditory pathway and generate a medically significant result. Thus, the augmented inspector interface system 102 can automatically present to the clinician, from a collection of available computing algorithms/operations, those computing algorithms/operations that are relevant to the recognized anatomical structure depicted in the medical image, which can eliminate the need for the clinician to wade through lists of potentially irrelevant algorithms/operations (e.g., endocardium-centric algorithms, heart-centric algorithms, cardio-vascular-centric algorithms, chest-centric algorithms, and PET-centric algorithms can be irrelevant to an MRI scan of a patient's auditory pathway).

Consider another, non-limiting example. Suppose that the medical image 104 is a PET scan of a patient's heart. In various aspects, the PET scan of the patient's heart can be electronically and/or digitally displayed to a clinician that desires to analyze, evaluate, examine, and/or inspect the PET scan of the patient's heart for diagnostic purposes. In various aspects, the magnification component 110 can generate and/or be implemented as a computerized, movable magnifying glass tool that is electronically displayed to the clinician and superimposed over the PET scan of the patient's heart. In various aspects, the clinician can position (e.g., via a computer mouse) the computerized, movable magnifying glass tool over a desired portion of the PET scan of the patient's heart. In various cases, the computerized, movable magnifying glass tool can magnify the desired portion of the PET scan of the patient's heart (e.g., can electronically and/or digitally display a magnified view of the portion of the PET scan of the patient's heart over which the computerized, magnifying glass tool is placed). Suppose that the clinician places the computerized, movable magnifying glass tool over a segment of the endocardium depicted in the PET scan of the patient's heart. Thus, the magnification component 110 (e.g., the computerized, movable magnifying glass tool) can electronically and/or digitally display a magnified view of the segment of the endocardium. In various aspects, the recognition component 112 can recognize an anatomical structure depicted in the magnified portion of the PET scan of the patient's heart. Since the magnified portion of the PET scan of the patient's heart can primarily depict the segment of the endocardium over which the clinician placed the computerized, movable magnifying glass tool, the recognition component 112 (e.g., via a trained machine learning classifier) can recognize, determine, and/or infer that the magnified portion of the PET scan of the patient's heart depicts a segment of the endocardium. In various embodiments, the recommendation component 114 can recommend one or more sets of computing algorithms and/or computer operations based on the recognized anatomical structure. Since the recognition component 112 recognized that the magnified portion of the PET scan of the patient's heart depicts a segment of the endocardium, the recommendation component 114 can recommend/suggest one or more sets of computing algorithms and/or computing operations that are related and/or relevant to medical analysis of endocardia. For example, the recommendation component 114 can recommend (e.g., via an ontology and/or mapping that links anatomical structures to relevant algorithms/operations) endocardium-centric algorithms (e.g., endocardium tracking algorithms, endocardium diagnostic algorithms, endocardium prognostic algorithms, endocardium treatment algorithms), heart-centric algorithms, cardio-vascular-centric algorithms, chest-centric algorithms, PET-centric algorithms, and/or any other relevant and/or related algorithms that can analyze the PET scan of the patient's heart and generate a medically significant result. Thus, the augmented inspector interface system 102 can automatically present to the clinician, from a collection of available computing algorithms/operations, those computing algorithms/operations that are relevant to the recognized anatomical structure depicted in the medical image, which can eliminate the need for the clinician to wade through lists of potentially irrelevant algorithms/operations (e.g., cochlea-centric algorithms, auditory-pathway-centric algorithms, ear-centric algorithms, head-centric algorithms, and MRI-centric algorithms can be irrelevant to a PET scan that depicts a heart of a patient).

As shown by these illustrative, non-limiting examples, embodiments of the augmented inspector interface system 102 can be implemented as an enhanced inspection tool usable by a clinician to more quickly and efficiently analyze, evaluate, and/or inspect the medical image 104 (e.g., the augmented inspector interface system 102 can automatically recognize a depicted anatomical structure in the medical image 104 and can automatically recommend relevant computing algorithms/operations to be executed on the medical image 104, such that the clinician does not need to waste time determining and/or searching for relevant computing algorithms/operations).

Figure 2:
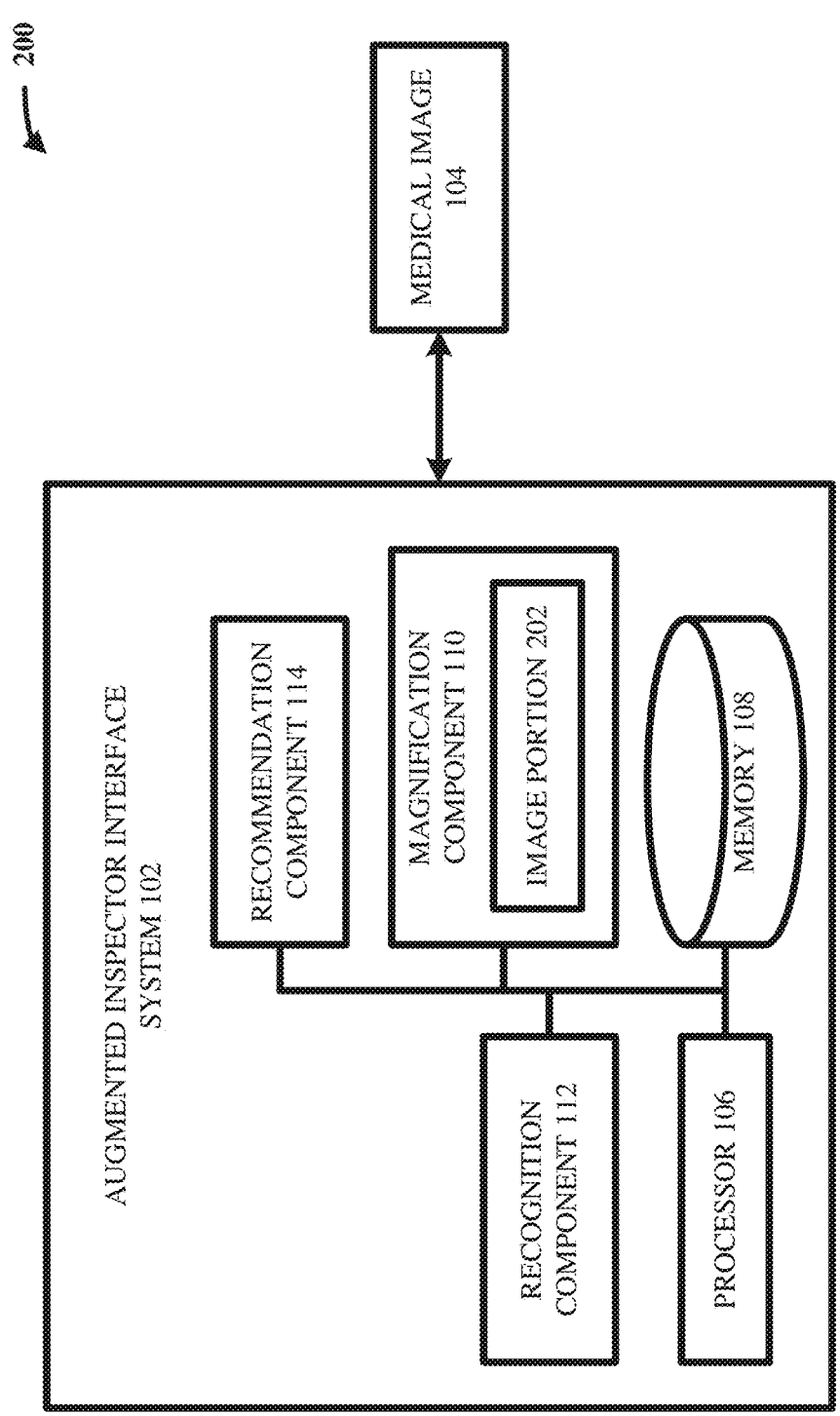
FIG. 2 illustrates a block diagram of an example, non-limiting system including an image portion that facilitates an augmented inspector interface with targeted, context-driven algorithms in accordance with one or more embodiments described herein.

FIG. 2 illustrates a block diagram of an example, non-limiting system 200 including an image portion that can facilitate an augmented inspector interface with targeted, context-driven algorithms in accordance with one or more embodiments described herein. As shown, the system 200 can, in various embodiments, comprise the same components as the system 100, and can further comprise an image portion 202.

As explained above, the magnification component 110 can, in various aspects, magnify a desired portion of the medical image 104 (e.g., the clinician can place/move the computerized, movable magnifying glass tool over top of a desired portion of the medical image 104). In various aspects, the result can be the image portion 202. In other words, the image portion 202 can, in various cases, be the portion of the medical image 104 that is magnified by the magnification component 110. In various aspects, the image portion 202 can contain fewer pixels and/or voxels than the medical image 104. As explained herein, the image portion 202 can represent a portion of the medical image 104 that the clinician desires to analyze, evaluate, and/or inspect (e.g., the clinician can move/place the computerized, movable magnifying glass tool over a portion of interest of the medical image 104, and that portion of interest can be the image portion 202). In various cases, the image portion 202 can depict one or more anatomical structures (e.g., can depict one or more body parts of a patient that the clinician desires to analyze, evaluate, and/or inspect).

Figure 3:
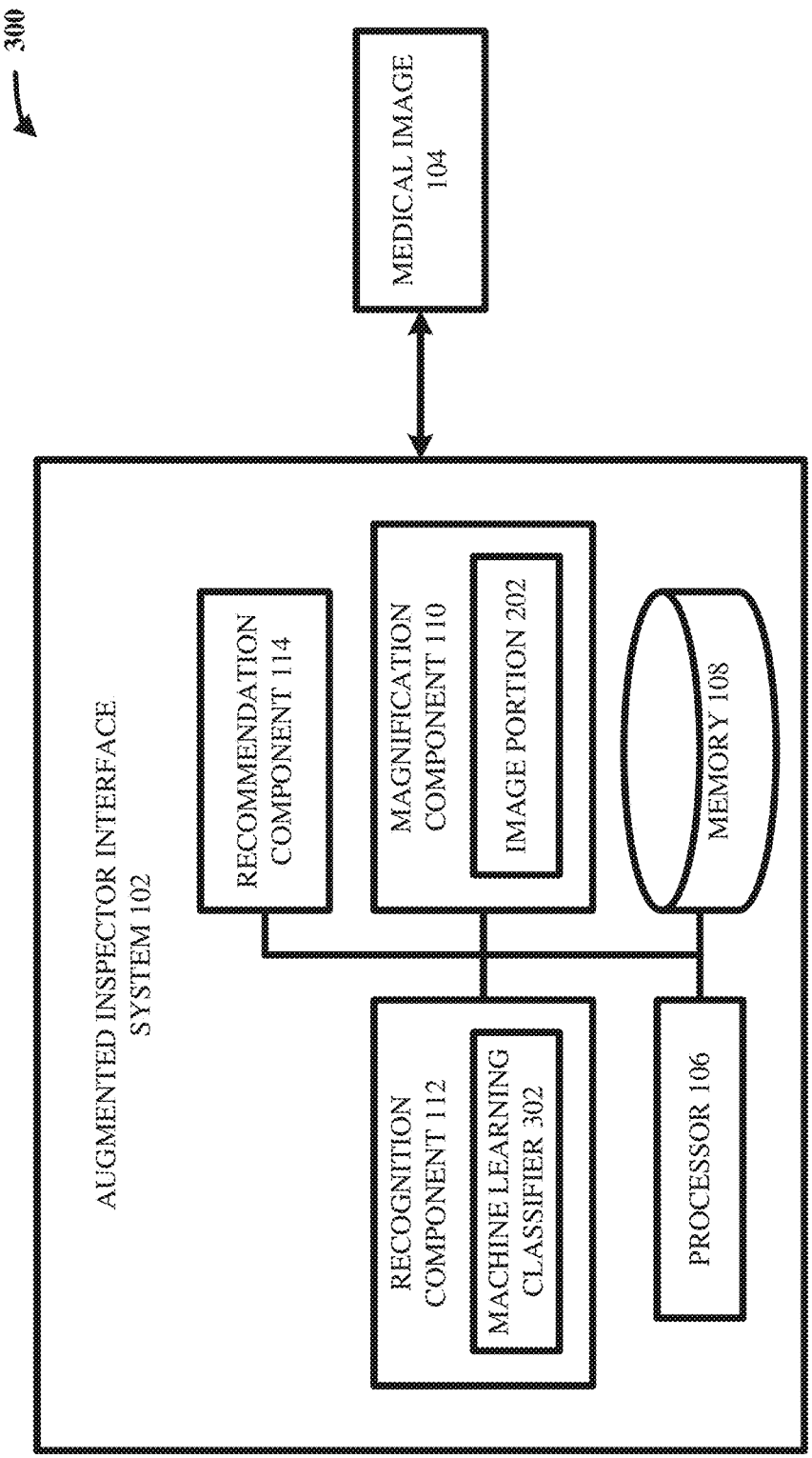
FIG. 3 illustrates a block diagram of an example, non-limiting system including a machine learning classifier that facilitates an augmented inspector interface with targeted, context-driven algorithms in accordance with one or more embodiments described herein.

FIG. 3 illustrates a block diagram of an example, non-limiting system 300 including a machine learning classifier that can facilitate an augmented inspector interface with targeted, context-driven algorithms in accordance with one or more embodiments described herein. As shown, the system 300 can, in various aspects, comprise the same components as the system 200, and can further comprise a machine learning classifier 302.

As explained above, the recognition component 112 can, in various embodiments, employ the machine learning classifier 302 to recognize one or more anatomical structures depicted in the image portion 202. In various instances, the machine learning classifier 302 can leverage any suitable artificial intelligence, machine learning, and/or deep learning classification/labeling paradigm (e.g., linear and/or non-linear classifiers). In various aspects, the machine learning classifier 302 can be trained via any suitable training technique (e.g., supervised learning, unsupervised learning, reinforcement learning). In some embodiments, the machine learning classifier 302 can be trained to receive as input the image portion 202 and to generate as output a classification/label that identifies one or more anatomical structures depicted/illustrated in the image portion 202 (e.g., in some cases, the machine learning classifier 302 can be trained to implement image recognition and/or computer vision). In some embodiments, the machine learning classifier 302 can be trained to receive metadata (e.g., DICOM metadata) characterizing the image portion 202 and/or the medical image 104 and generate as output a classification/label that identifies one or more anatomical structures depicted/illustrated in the image portion 202 (e.g., in some cases, the machine learning classifier 302 can be trained to implement metadata recognition). In various embodiments, the machine learning classifier 302 can be trained to receive as input both the image portion 202 and metadata pertaining to the image portion 202 and/or the medical image 104 and generate as output a classification/label that identifies one or more anatomical structures depicted in the image portion 202.

To facilitate some of the above-described machine learning aspects of various embodiments of the subject innovation, consider the following discussion of artificial intelligence. Various embodiments of the present innovation herein can employ artificial intelligence (AI) to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z1, z2, z3, z4, zn)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Figure 4:
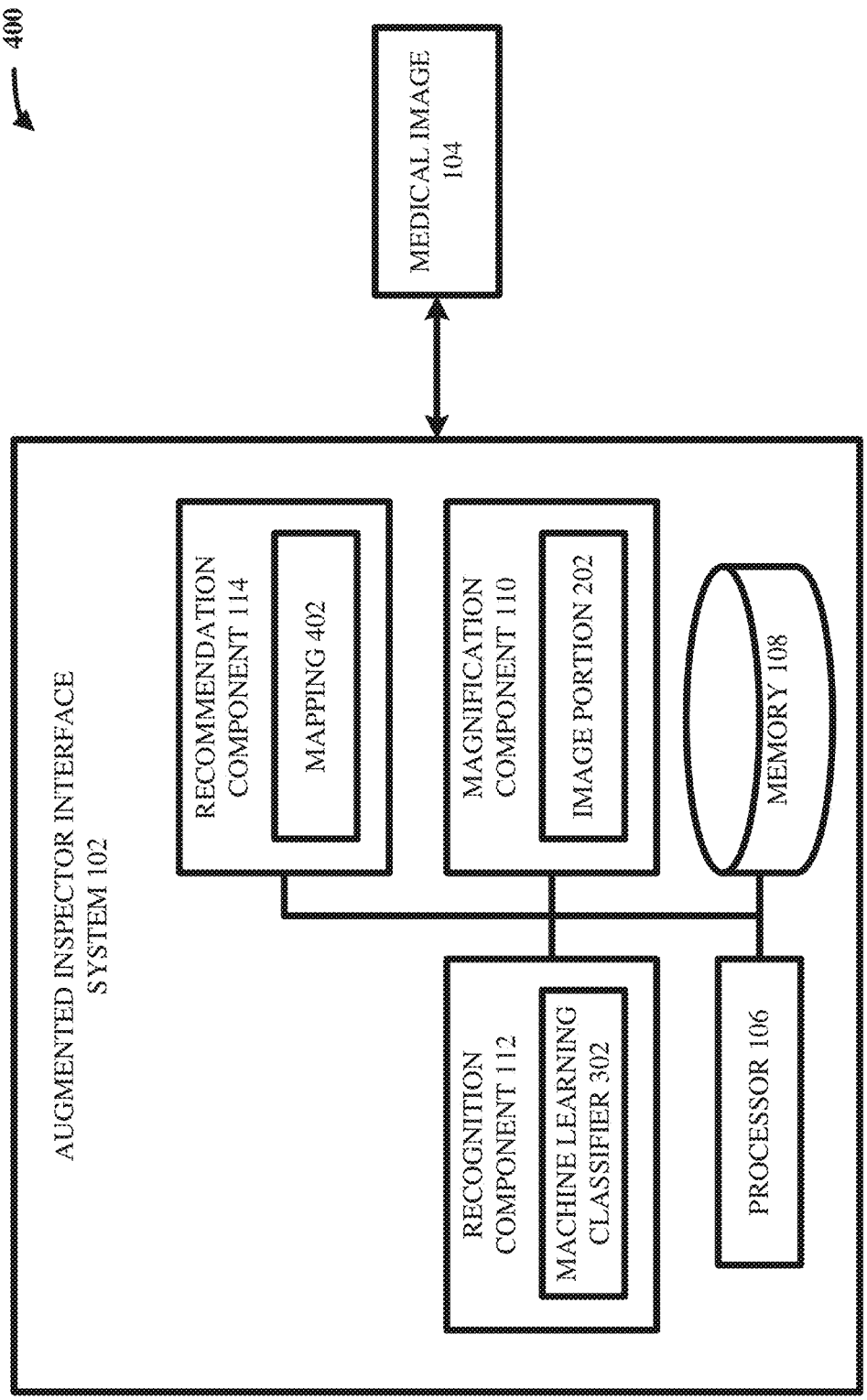
FIG. 4 illustrates a block diagram of an example, non-limiting system including a mapping that facilitates an augmented inspector interface with targeted, context-driven algorithms in accordance with one or more embodiments described herein.

FIG. 4 illustrates a block diagram of an example, non-limiting system 400 including a mapping that can facilitate an augmented inspector interface with targeted, context-driven algorithms in accordance with one or more embodiments described herein. As shown, the system 400 can, in various embodiments, comprise the same components as the system 300, and can further comprise a mapping 402.

In various embodiments, the recommendation component 114 can leverage the mapping 402 to recommend/suggest one or more sets of computing algorithms and/or computing operations that are related to and/or relevant to the one or more recognized anatomical structures identified by the recognition component 112. In various instances, the mapping 402 can be considered an ontology and/or decision tree that links and/or maps one or more anatomical structures to one or more related computing algorithms and/or computing operations. In various aspects, there can exist a library (e.g., centralized and/or distributed collection) containing available computing algorithms and/or computing operations that can be executed on the medical image 104 (and/or a portion thereof) to generate medically significant results (e.g., feature tracking algorithms, diagnosis-generating algorithms, prognosis-generating algorithms, treatment-option-generating algorithms). In various aspects, depending on the particular anatomical structures depicted in medical image 104, only one or more subsets of the total library of computing algorithms/operations can be relevant and/or useful for analyzing, evaluating, and/or inspecting the medical image 104 (e.g., cochlea-centric algorithms can be irrelevant to analyze, evaluate, and/or inspect medical images that primarily depict cardiovascular structures; respiratory-centric algorithms can be irrelevant to analyze, evaluate, and/or inspect medical images that primarily depict skeletal structures; brain-centric algorithms can be irrelevant to analyze, evaluate, and/or inspect medical images that primarily depict skin lesions). Conventionally, a clinician would have to wade through the entire library to search for potentially applicable algorithms/operations, which can waste time. As explained herein, however, the recommendation component 114 can, in various instances, leverage the mapping 402 to automatically suggest, recommend, and/or identify for the clinician those subsets of related and/or relevant algorithms/operations, based on the one or more anatomical structures recognized by the recognition component 112.

As an illustrative, non-limiting example, consider a library of available computing algorithms (and/or other computing operations) that includes the following: alveoli-centric algorithms (e.g., algorithms designed to provide feature tracking capabilities, diagnostic capabilities, prognostic capabilities, treatment-generation capabilities, and/or any other suitable capabilities with respect to alveoli specifically); bronchi-centric algorithms (e.g., algorithms designed to provide feature tracking, diagnoses, prognoses, and/or treatment options with respect to bronchi specifically); lung-centric algorithms (e.g., algorithms designed to provide feature tracking, diagnoses, prognoses, and/or treatment options with respect to the lungs generally); ventricle-centric algorithms (e.g., algorithms designed to provide feature tracking, diagnoses, prognoses, and/or treatment options with respect to the ventricles specifically); endocardium-centric algorithms (e.g., algorithms designed to provide feature tracking, diagnoses, prognoses, and/or treatment options with respect to the endocardium specifically); heart-centric algorithms (e.g., algorithms designed to provide feature tracking, diagnoses, prognoses, and/or treatment options with respect to the heart generally); and chest-centric algorithms (e.g., algorithms designed to provide feature tracking, diagnoses, prognoses, and/or treatment options with respect to the chest generally). In various aspects, the mapping 402 can map/link anatomical structures to related/relevant algorithms in this library. For example, the mapping 402 can map an alveoli to alveoli-centric algorithms, lung-centric algorithms, and/or chest-algorithms (e.g., the alveolae are anatomical structures in the lungs, which are in the chest). Similarly, the mapping 402 can map a bronchi to the bronchi-centric algorithms, the lung-centric algorithms, and/or the chest-centric algorithms (e.g., the bronchi are anatomical structures in the lungs, which are in the chest). Moreover, the mapping 402 can map a ventricle to the ventricle-centric algorithms, the heart-centric algorithms, and/or the chest-centric algorithms (e.g., a ventricle is an anatomical structure in the heart, which is in the chest). Similarly, the mapping 402 can map an endocardium to the endocardium-centric algorithms, the heart-centric algorithms, and the chest-centric algorithms (e.g., the endocardium is an anatomical structure in the heart, which is in the chest).

In this way, the recommendation component 114 can, via the mapping 402, quickly identify for the clinician and/or provide at the clinician's fingertips the available computing algorithms/operations that are relevant to the one or more anatomical structures depicted in the image portion 202 (e.g., such that the clinician does not need to waste time and/or resources considering irrelevant computing algorithms/operations). In other words, the augmented inspector interface system 102 can, in various embodiments, recommend to a clinician relevant computational algorithms/operations based on an automatically recognized context (e.g., the recognized anatomical structures) of the image portion 202.

Figure 5:
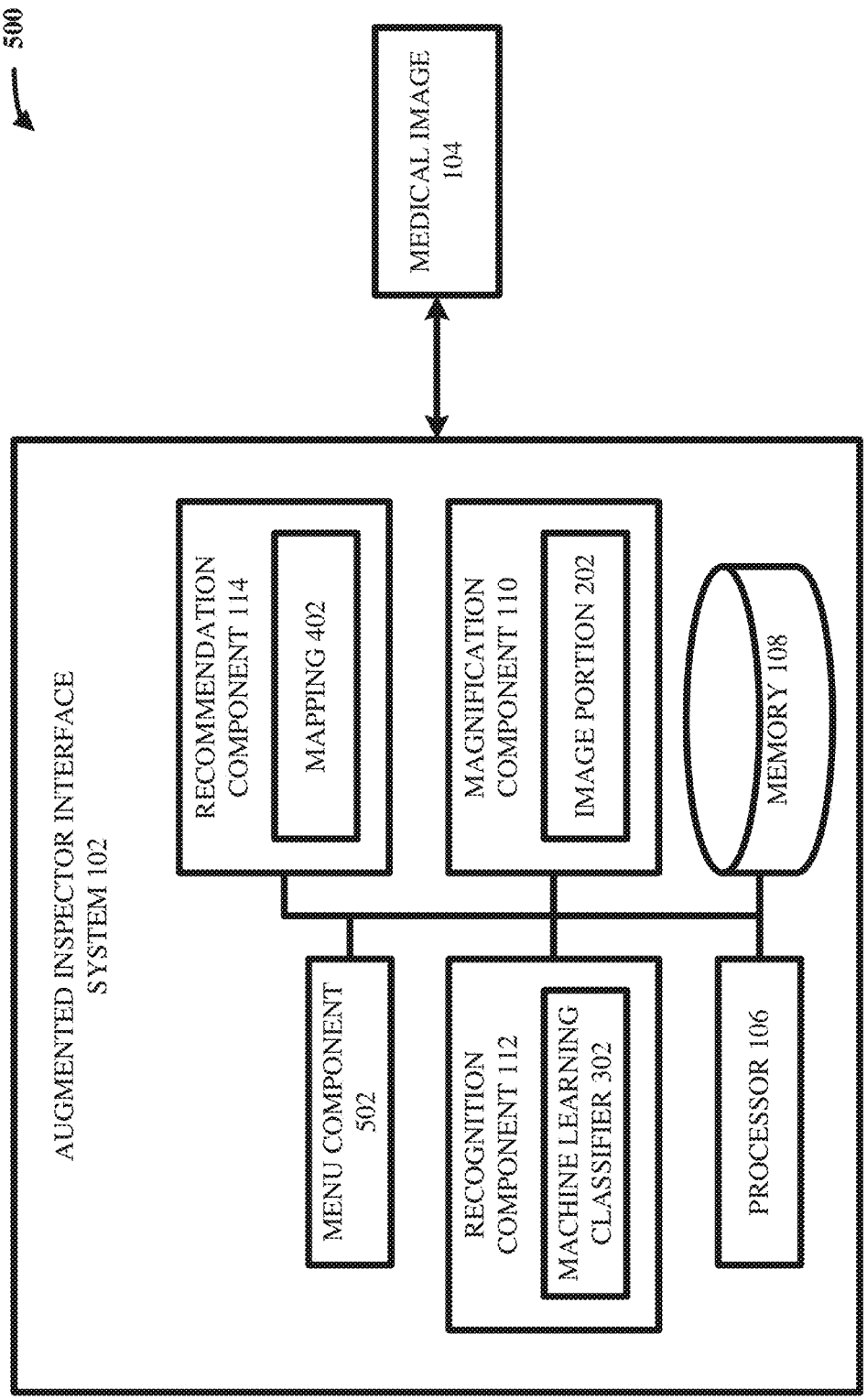
FIG. 5 illustrates a block diagram of an example, non-limiting system including a menu component that facilitates an augmented inspector interface with targeted, context-driven algorithms in accordance with one or more embodiments described herein.

FIG. 5 illustrates a block diagram of an example, non-limiting system 500 including a menu component that can facilitate an augmented inspector interface with targeted, context-driven algorithms in accordance with one or more embodiments described herein. As shown, the system 500 can, in various instances, comprise the same components as the system 400, and can further comprise a menu component 502.

In various embodiments, the menu component 502 can display (e.g., via the electronic and/or digital computer screen and/or monitor on which the medical image 104 is displayed and on which the image portion 202 is displayed) the one or more recommended sets of computing algorithms and/or computing operations in a drop-down menu. In various aspects, the drop-down menu can be displayed as adjacent to the image portion 202 and/or adjacent to the computerized, movable magnifying glass tool generated by the magnification component 110. In various aspects, the drop-down menu can list the one or more recommended sets of computing operations and/or computing algorithms in order of specificity (e.g., from most specific to most general; and/or from most general to most specific). In various aspects, the drop-down menu can be oriented vertically (e.g., most specific computing algorithms/operations listed near the top of the drop-down menu, most general computing algorithms/operations listed near the bottom of the drop-down menu). In various aspects, the drop-down menu can be oriented horizontally (e.g., most specific computing algorithms/operations listed near the left of the drop-down menu, most general computing algorithms/operation listed near the right of the drop-down menu). In various aspects, the drop-down menu can exhibit any suitable display configuration and/or arrangement.

Figure 6:
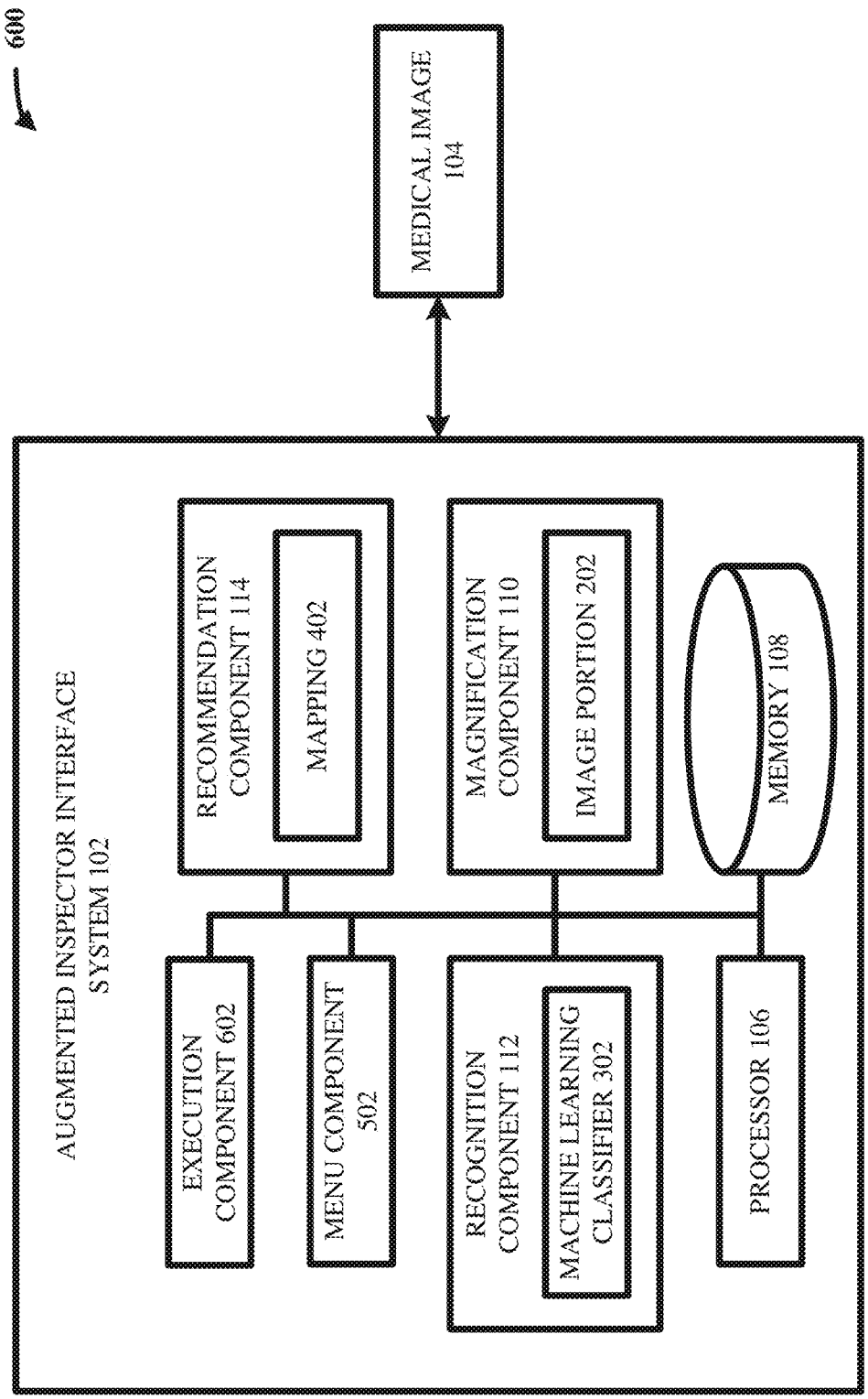
FIG. 6 illustrates a block diagram of an example, non-limiting system including an execution component that facilitates an augmented inspector interface with targeted, context-driven algorithms in accordance with one or more embodiments described herein.

FIG. 6 illustrates a block diagram of an example, non-limiting system 600 including an execution component that can facilitate an augmented inspector interface with targeted, context-driven algorithms in accordance with one or more embodiments described herein. As shown, the system 600 can, in various cases, comprise the same components as the system 500, and can further comprise an execution component 602.

In various embodiments, the execution component 602 can execute a computing algorithm and/or computing operation selected from the one or more recommended sets of computing algorithms and/or computing operations. In various aspects, the clinician can select (e.g., via a computer mouse and/or any other suitable human-computer interface device) a computing algorithm/operation from the drop-down menu. In various instances, the execution component 602 can execute the selected computing algorithm/operation on the image portion 202 rather than on the entirety of the medical image 104. In other words, the execution component 602 can feed the image portion 202 as input to the selected computing algorithm/operation rather than feeding the entire medical image 104 as input to the selected computing algorithm/operation. This can cause the selected computing algorithm/operation to computationally operate on the image portion 202 (e.g., to execute on the magnified portion of the medical image 104) and to computationally ignore the remainder of the medical image 104 (e.g., to not execute on the unmagnified portion of the medical image 104). In various aspects, this can be considered as spatial targeting and/or localization of the selected computing algorithm/operation. That is, the execution component 602 can target and/or localize the selected computing algorithm/operation such that it executes only on the image portion 202 and not on the full medical image 104. In various embodiments, such spatial targeting and/or localization can speed up the execution of the selected computing algorithm/operation. After all, the image portion 202 can be smaller (e.g., can have fewer pixels and/or voxels) than the medical image 104. Thus, the selected computing algorithm/operation can execute more quickly on the image portion 202 than it can on the medical image 104 (e.g., an input size/volume that is fed to the selected computing algorithm/operation can be decreased by spatial targeting/localization, which can decrease compute power and/or compute time required to execute the selected computing algorithm/operation).

FIGS. 7-10 illustrate exemplary, non-limiting screenshots 700-1000 of an augmented inspector interface with targeted, context-driven algorithms in accordance with one or more embodiments described herein. In various instances, FIGS. 7-10 depict screenshots of non-limiting, exemplary implementations of embodiments of the subject innovation.

Figure 7:
FIGS. 7-10 illustrate exemplary, non-limiting screenshots of an augmented inspector interface with targeted, context-driven algorithms in accordance with one or more embodiments described herein.

As shown in FIG. 7, the screenshot 700 depicts a CT scan 702 of an axial-cross-section of a patient's lungs. In various embodiments, the CT scan 702 can be considered as analogous to the medical image 104. As shown in FIG. 7, the screenshot 700 depicts a magnified portion 704 of the CT scan 702. In various embodiments, the magnified portion 704 can be considered as analogous to the image portion 202. As shown in FIG. 7, the screenshot 700 depicts a cursor 708. In various aspects, the cursor 708 can be used by the clinician (e.g., via a computer mouse and/or any other suitable human-computer interface device) to select the portion of the CT scan 702 that is to be magnified. For example, the clinician can use the cursor 708 to launch the augmented inspector interface system 102 from a computer toolbar, and can use the cursor 708 to move a computerized, movable magnifying glass tool corresponding to the augmented inspector interface system 102 over the portion of the CT scan 702 that is desired to be magnified. In various aspects, as shown, the magnified portion 704 can depict a lymph node 706. In various aspects, the lymph node 706 can be considered as analogous to the anatomical structure depicted in the image portion 202.

Figure 8:
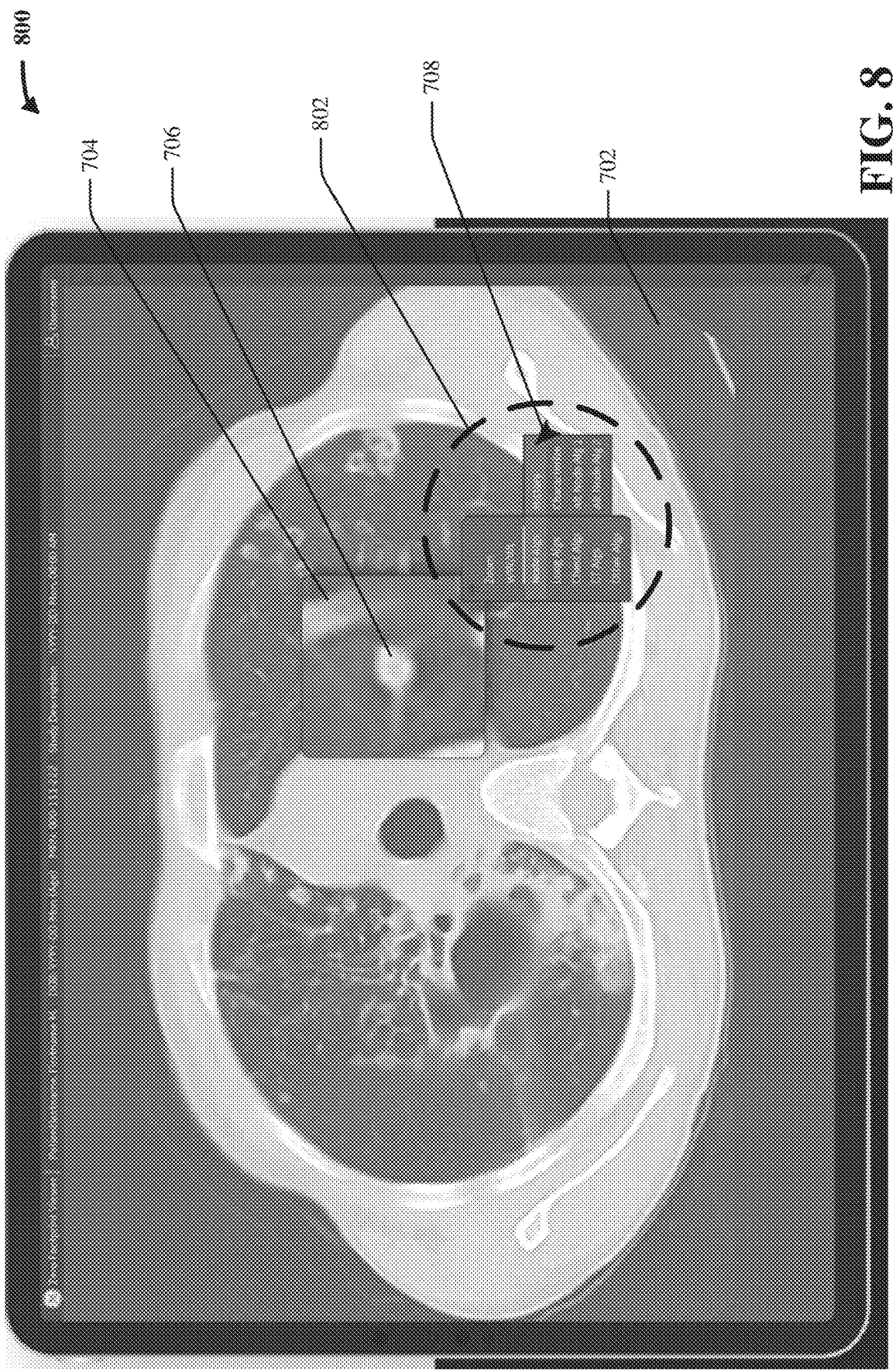

As shown in FIG. 8, the screenshot 800 depicts a drop-down menu 802 that lists one or more contextually-driven, recommended computing algorithms and/or computing operations that can be executed on the CT scan 702 and/or the magnified portion 704. As explained above, the recognition component 112 can, via the machine learning classifier 302, recognize, determine, and/or infer that the magnified portion 704 depicts/illustrates the lymph node 706. Accordingly, the recommendation component 114 can, via the mapping 402, recommend and/or suggest one or more computing algorithms and/or computing operations to execute on the CT scan 702 and/or the magnified portion 704 based on the lymph node 706 (e.g., can recommend that lymph-node-centric algorithms, lung-centric algorithms, and/or chest-centric algorithms be executed on the CT scan 702 and/or the magnified portion 704). In various instances, these one or more recommended sets of computing algorithms and/or computing operations can be displayed in the drop-down menu 802 (e.g., generated by the menu component 502). As shown in the illustrated example, the drop-down menu 802 can list a "zoom" computing operation, a "WW/WL" (window width/window length) computing operation, and/or any other suitable standard inspection operations. Also as shown, the drop-down menu 802 can list a selectable button for lymph node algorithms (e.g., "node algs"), a selectable button for lung algorithms (e.g., "lung algs"), a selectable button for chest algorithms (e.g., "chest algs"), a selectable button for CT algorithms (e.g., "CT algs"), and a selectable button for other algorithms (e.g., "other algs"). As explained above, these algorithms can be suggested by the recommendation component 114 based on the context of the CT scan 702 (e.g., these algorithms are relevant to lymph nodes and can be suggested/recommended based on the fact that the magnified portion 704 depicts the lymph node 706). In various embodiments, as shown, the clinician can use the cursor 708 to select the button representing lymph node algorithms, which can, in some cases, correspondingly open a second drop-down menu that lists specific lymph-node-centric algorithms that can be executed on the CT scan 702 and/or the magnified portion 704. Such specific lymph-node-centric algorithms can include, for example, a "history" algorithm (e.g., feature tracking) that can be trained to track the size of lymph nodes in a patient over time, and/or a "characterize" algorithm that can be trained to analyze the lymph nodes to generate diagnostic and/or prognostic information. Any other suitable lymph-node-centric algorithms can be included in various embodiments. As shown, the clinician can select the "history" algorithm to track a size of the lymph node 706 of the patient over time. As shown, in various aspects, the one or more sets of recommended computing algorithms and/or computing operations can be listed in the drop-down menu 802 in order of specificity and/or generality.

Figure 9:
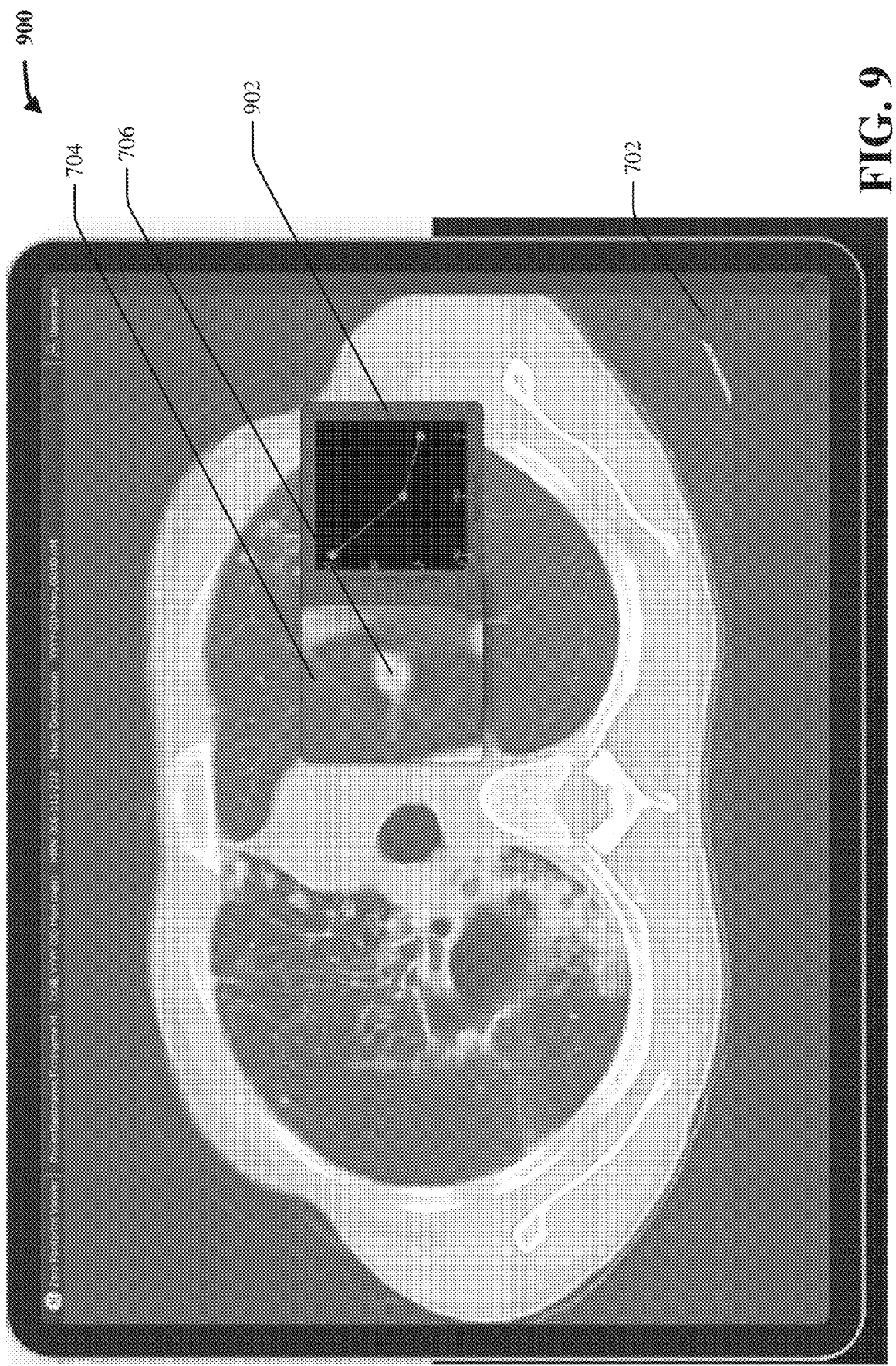

As shown in FIG. 9, the screenshot 900 depicts a results summary 902. In various aspects, the execution component 602 can execute a computing algorithm and/or computing operation selected from the drop-down menu 802 in a spatially localized and/or targeted fashion (e.g., such that the selected computing algorithm and/or computing operation executes only on the magnified portion 704 and not on the remaining, unmagnified portions of the CT scan 702). Once executed, the generated/outputted results of the selected computing algorithm and/or computing operation can be displayed in the results summary 902. In various instances, the configuration and/or content of the results summary 902 can depend on the type of analysis performed and/or results generated by the selected computing algorithm and/or computing operation. In the example depicted, the "history" algorithm can be a feature tracking algorithm that uses machine learning to identify relevant comparison studies and location of the lymph node 706 to generate the results summary 902 (e.g., the "history" algorithm can identify the lymph node 706 in prior CT scans of the same patient to determine how the size of the lymph node 706 has changed over time). In various aspects, the results summary 902 can be a chart that shows the change in size of the lymph node 706 over time. As shown in the depicted example, two previous CT scans from the same patient were taken (e.g., one take one month prior, another take two months prior). As shown in the results summary 902, the size of the lymph node 706 has decreased significantly from the two previous CT scans.

Figure 10:

As shown in FIG. 10, the screenshot 1000 depicts an animation 1002. In various aspects, the animation 1002 can be considered a "flip-book" of prior images of the lymph node 706 that can be played forward and/or backward. Thus, the change in size of the lymph node 706 can be viewed more easily by the clinician. In various aspects, the "history" algorithm can retrieve the relevant comparison studies/priors so that the clinician can "play" through them without having to manually find the studies/priors, without having to manually load the studies/priors into a viewport, and/or without having to manually scroll to the appropriate slices within the series. Thus, embodiments of the subject innovation can save the clinician time when analyzing, evaluating, and/or inspecting the CT scan 702.

In various aspects, it should be understood that the type, nature, and/or configuration of the animation 1002 can depend on the type of analysis performed by and/or results generated by the selected computing algorithm and/or computing operation. In some cases, a selected computing algorithm and/or computing operation can perform an analysis and/or generate a result that cannot be displayed as an animation.

Figure 11:
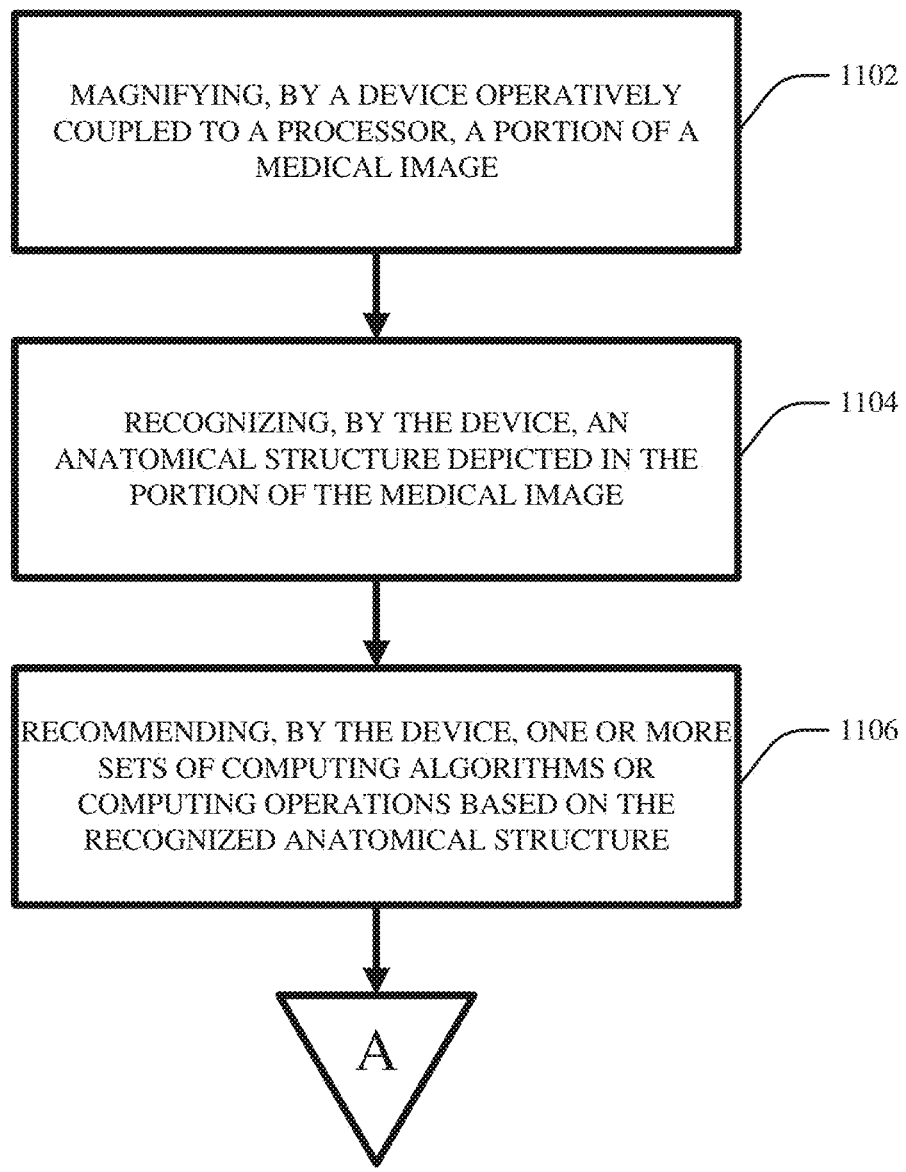
FIG. 11 illustrates a flow diagram of an example, non-limiting computer-implemented method that facilitates an augmented inspector interface with targeted, context-driven algorithms in accordance with one or more embodiments described herein.

FIG. 11 illustrates a flow diagram of an example, non-limiting computer-implemented method 1100 that can facilitate an augmented inspector interface with targeted, context-driven algorithms in accordance with one or more embodiments described herein.

In various embodiments, act 1102 can include magnifying, by a device operatively coupled to a processor (e.g., 110), a portion (e.g., 202 and/or 704) of a medical image (e.g., 104 and/or 702).

In various aspects, act 1104 can include recognizing, by the device (e.g., 112 and/or 302), an anatomical structure (e.g., 706) depicted in the portion of the medical image.

In various instances, act 1106 can include recommending, by the device (e.g., 114 and/or 402), one or more sets of computing algorithms and/or computing operations based on the recognized anatomical structure.

Figure 12:
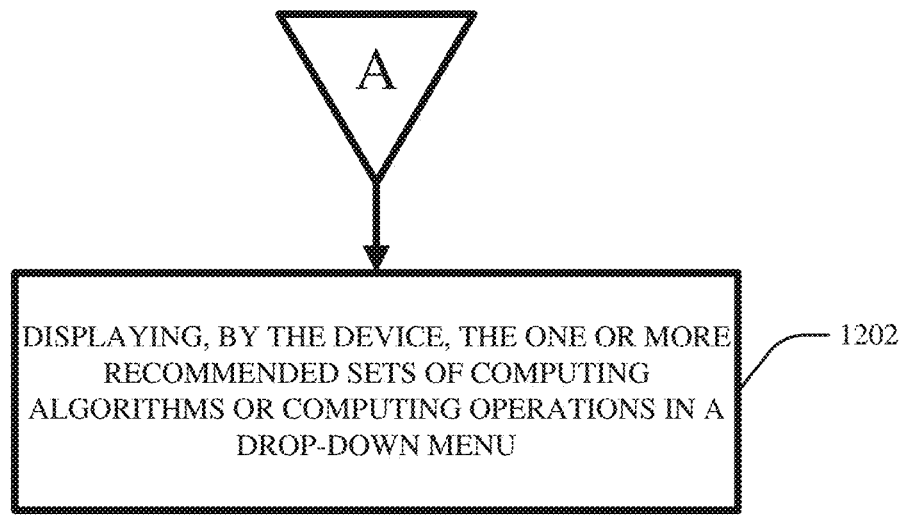
FIG. 12 illustrates a flow diagram of an example, non-limiting computer-implemented method including displaying a drop-down menu of recommended computing algorithms or computing operations that facilitates an augmented inspector interface with targeted, context-driven algorithms in accordance with one or more embodiments described herein.

FIG. 12 illustrates a flow diagram of an example, non-limiting computer-implemented method 1200 including displaying a drop-down menu of recommended computing algorithms or computing operations that can facilitate an augmented inspector interface with targeted, context-driven algorithms in accordance with one or more embodiments described herein.

In various cases, act 1202 can include displaying, by the device (e.g., 502), the one or more recommended sets of computing algorithms or computing operations in a drop-down menu (e.g., 802).

Figure 13:
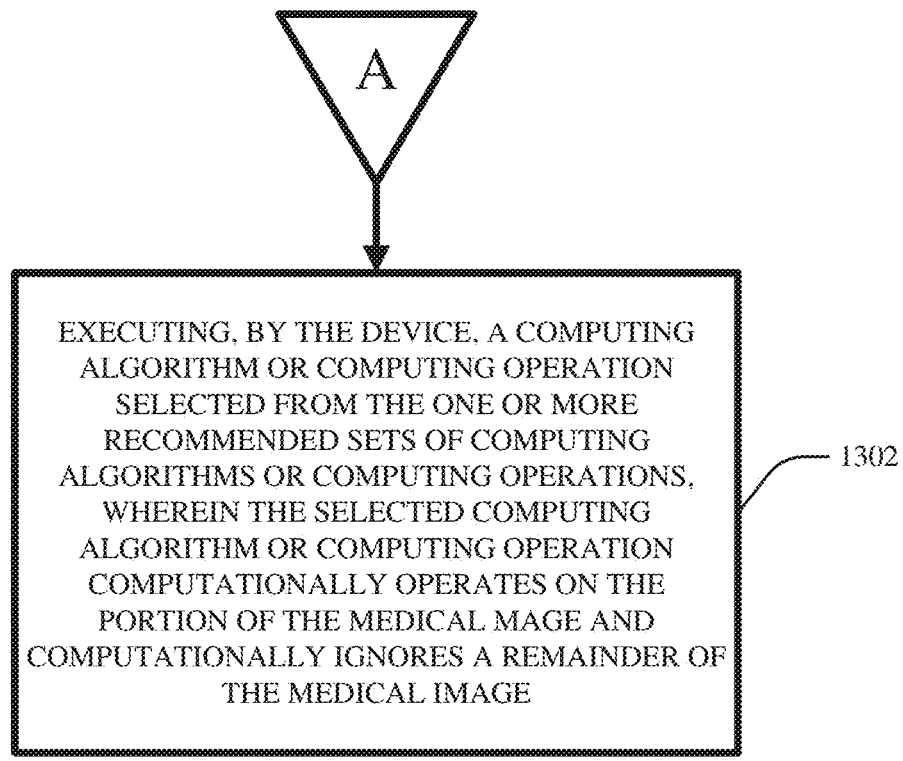
FIG. 13 illustrates a flow diagram of an example, non-limiting computer-implemented method including executing a selected computing algorithm or computing operation that facilitates an augmented inspector interface with targeted, context-driven algorithms in accordance with one or more embodiments described herein.

FIG. 13 illustrates a flow diagram of an example, non-limiting computer-implemented method 1300 including executing a selected computing algorithm or computing operation that can facilitate an augmented inspector interface with targeted, context-driven algorithms in accordance with one or more embodiments described herein.

In various embodiments, act 1302 can include executing, by the device (e.g., 602), a computing algorithm or computing operation selected from the one or more recommended sets of computing algorithms or computing operations, wherein the selected computing algorithm or computing operation computationally operates on the portion of the medical image and computationally ignores a remainder of the medical image.

Figure 14:
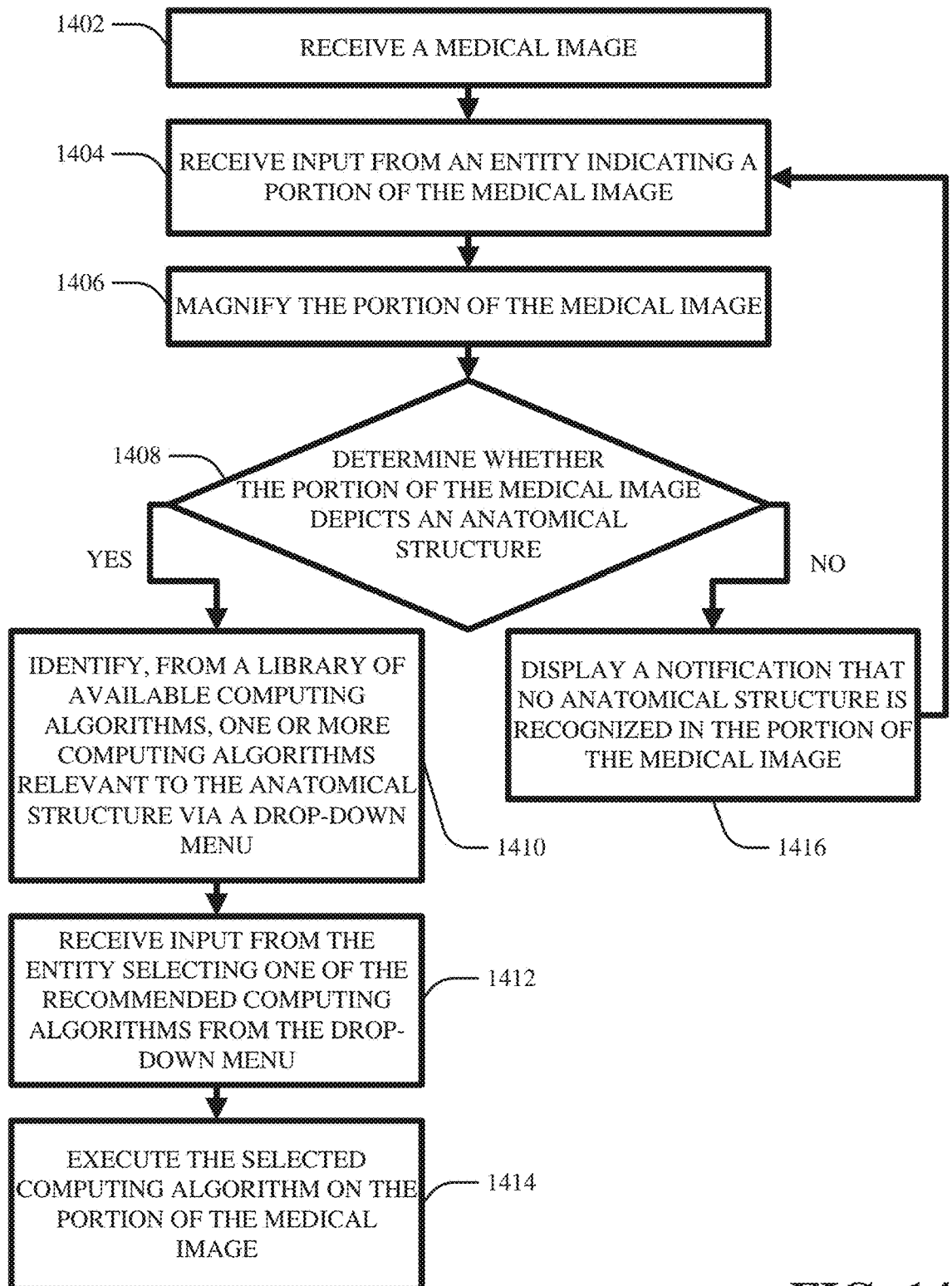
FIG. 14 illustrates a flow diagram of an example, non-limiting computer implemented method that facilitates an augmented inspector interface with targeted, context-driven algorithms in accordance with one or more embodiments described herein.

FIG. 14 illustrates a flow diagram of an example, non-limiting computer implemented method that can facilitate an augmented inspector interface with targeted, context-driven algorithms in accordance with one or more embodiments described herein.

In various embodiments, act 1402 can include receiving (e.g., by a device operatively coupled to a processor) a medical image (e.g., 104 and/or 702).

In various aspects, act 1404 can include receiving (e.g., by the device) input from an entity (e.g., clinician, radiologist, and/or any other suitable health care provider, human and/or otherwise) indicating a portion of the medical image (e.g., 202 and/or 704). In various cases, the entity can provide such input through any suitable interface apparatus such as a computer mouse, joystick, keyboard, keypad, and/or motion capture.

In various instances, act 1406 can include magnifying (e.g., by the device) the portion of the medical image. In various cases, this can be facilitated by the magnification component 110.

In various embodiments, act 1408 can include determining (e.g., by the device) whether the portion of the medical image depicts an anatomical structure (e.g., 706). If YES, acts 1410-1414 can be executed. If NO, act 1416 can be executed. In various cases, act 1408 can be facilitated by the recognition component 112.

In various aspects, act 1410 can include identifying (e.g., by the device), from a library of available computing algorithms, one or more computing algorithms that are relevant to the anatomical structure via a drop-down menu (e.g., 802). In various cases, this can be facilitated by the recommendation component 114 and/or the menu component 502.

In various instances, act 1412 can include receiving (e.g., by the device) input from the entity selecting one of the recommended computing algorithms from the drop-down menu.

In various embodiments, act 1414 can include executing (e.g., by the device) the selected computing algorithm on the portion of the medical image. In various cases, this can be facilitated by the execution component 602.

In various aspects, act 1416 can include displaying (e.g., by the device) a notification that no anatomical structure is recognized in the portion of the medical image. In various aspects, this can cause a return to act 1404 (e.g., receiving new input from the entity indicating a new portion of the medical image to analyze, evaluate, and/or inspect).

Figure 15:
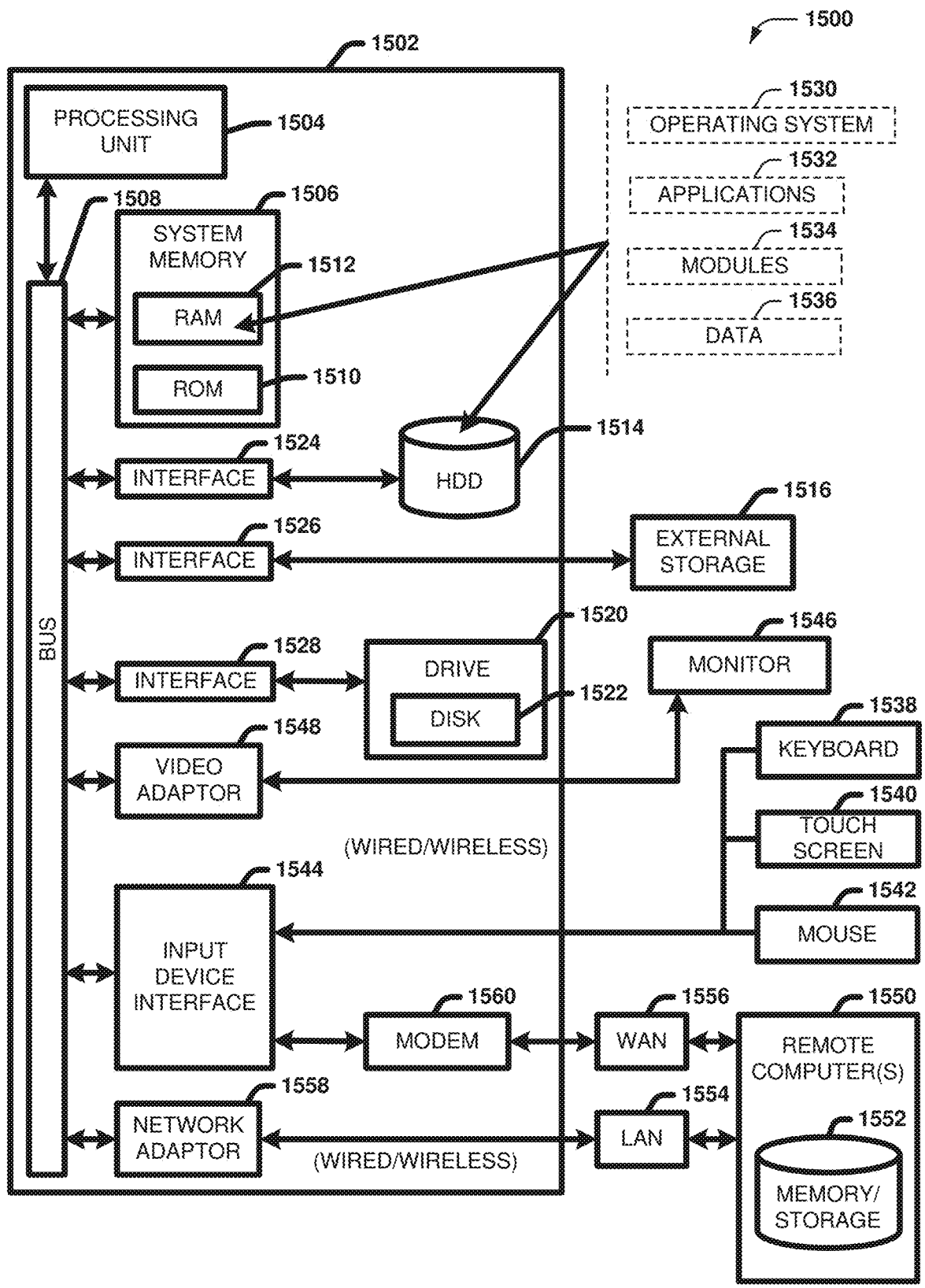
FIG. 15 illustrates a block diagram of an example, non-limiting operating environment in which one or more embodiments described herein can be facilitated.

In order to provide additional context for various embodiments described herein, FIG. 15 and the following discussion are intended to provide a brief, general description of a suitable computing environment 1500 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 15, the example environment 1500 for implementing various embodiments of the aspects described herein includes a computer 1502, the computer 1502 including a processing unit 1504, a system memory 1506 and a system bus 1508. The system bus 1508 couples system components including, but not limited to, the system memory 1506 to the processing unit 1504. The processing unit 1504 can be any of various commercially available processors. Dual microprocessors and other multi-processor architectures can also be employed as the processing unit 1504.

The system bus 1508 can be any of several types of bus structure that can further interconnect to a memory bus (with or without a memory controller), a peripheral bus, and a local bus using any of a variety of commercially available bus architectures. The system memory 1506 includes ROM 1510 and RAM 1512. A basic input/output system (BIOS) can be stored in a non-volatile memory such as ROM, erasable programmable read only memory (EPROM), EEPROM, which BIOS contains the basic routines that help to transfer information between elements within the computer 1502, such as during startup. The RAM 1512 can also include a high-speed RAM such as static RAM for caching data.

The computer 1502 further includes an internal hard disk drive (HDD) 1514 (e.g., EIDE, SATA), one or more external storage devices 1516 (e.g., a magnetic floppy disk drive (FDD) 1516, a memory stick or flash drive reader, a memory card reader, etc.) and a drive 1520, e.g., such as a solid state drive, an optical disk drive, which can read or write from a disk 1522, such as a CD-ROM disc, a DVD, a BD, etc. Alternatively, where a solid state drive is involved, disk 1522 would not be included, unless separate. While the internal HDD 1514 is illustrated as located within the computer 1502, the internal HDD 1514 can also be configured for external use in a suitable chassis (not shown). Additionally, while not shown in environment 1500, a solid state drive (SSD) could be used in addition to, or in place of, an HDD 1514. The HDD 1514, external storage device(s) 1516 and drive 1520 can be connected to the system bus 1508 by an HDD interface 1524, an external storage interface 1526 and a drive interface 1528, respectively. The interface 1524 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1502, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1512, including an operating system 1530, one or more application programs 1532, other program modules 1534 and program data 1536. All or portions of the operating system, applications, modules, and/or data can also be cached in the RAM 1512. The systems and methods described herein can be implemented utilizing various commercially available operating systems or combinations of operating systems.

Computer 1502 can optionally comprise emulation technologies. For example, a hypervisor (not shown) or other intermediary can emulate a hardware environment for operating system 1530, and the emulated hardware can optionally be different from the hardware illustrated in FIG. 15. In such an embodiment, operating system 1530 can comprise one virtual machine (VM) of multiple VMs hosted at computer 1502. Furthermore, operating system 1530 can provide runtime environments, such as the Java runtime environment or the .NET framework, for applications 1532. Runtime environments are consistent execution environments that allow applications 1532 to run on any operating system that includes the runtime environment. Similarly, operating system 1530 can support containers, and applications 1532 can be in the form of containers, which are lightweight, standalone, executable packages of software that include, e.g., code, runtime, system tools, system libraries and settings for an application.

Further, computer 1502 can be enable with a security module, such as a trusted processing module (TPM). For instance with a TPM, boot components hash next in time boot components, and wait for a match of results to secured values, before loading a next boot component. This process can take place at any layer in the code execution stack of computer 1502, e.g., applied at the application execution level or at the operating system (OS) kernel level, thereby enabling security at any level of code execution.

A user can enter commands and information into the computer 1502 through one or more wired/wireless input devices, e.g., a keyboard 1538, a touch screen 1540, and a pointing device, such as a mouse 1542. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1504 through an input device interface 1544 that can be coupled to the system bus 1508, but can be connected by other interfaces, such as a parallel port, an IEEE 1394 serial port, a game port, a USB port, an IR interface, a BLUETOOTH® interface, etc.

A monitor 1546 or other type of display device can be also connected to the system bus 1508 via an interface, such as a video adapter 1548. In addition to the monitor 1546, a computer typically includes other peripheral output devices (not shown), such as speakers, printers, etc.

The computer 1502 can operate in a networked environment using logical connections via wired and/or wireless communications to one or more remote computers, such as a remote computer(s) 1550. The remote computer(s) 1550 can be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1552 is illustrated. The logical connections depicted include wired/wireless connectivity to a local area network (LAN) 1554 and/or larger networks, e.g., a wide area network (WAN) 1556. Such LAN and WAN networking environments are commonplace in offices and companies, and facilitate enterprise-wide computer networks, such as intranets, all of which can connect to a global communications network, e.g., the Internet.

When used in a LAN networking environment, the computer 1502 can be connected to the local network 1554 through a wired and/or wireless communication network interface or adapter 1558. The adapter 1558 can facilitate wired or wireless communication to the LAN 1554, which can also include a wireless access point (AP) disposed thereon for communicating with the adapter 1558 in a wireless mode.

When used in a WAN networking environment, the computer 1502 can include a modem 1560 or can be connected to a communications server on the WAN 1556 via other means for establishing communications over the WAN 1556, such as by way of the Internet. The modem 1560, which can be internal or external and a wired or wireless device, can be connected to the system bus 1508 via the input device interface 1544. In a networked environment, program modules depicted relative to the computer 1502 or portions thereof, can be stored in the remote memory/storage device 1552. It will be appreciated that the network connections shown are example and other means of establishing a communications link between the computers can be used.

When used in either a LAN or WAN networking environment, the computer 1502 can access cloud storage systems or other network-based storage systems in addition to, or in place of, external storage devices 1516 as described above, such as but not limited to a network virtual machine providing one or more aspects of storage or processing of information. Generally, a connection between the computer 1502 and a cloud storage system can be established over a LAN 1554 or WAN 1556 e.g., by the adapter 1558 or modem 1560, respectively. Upon connecting the computer 1502 to an associated cloud storage system, the external storage interface 1526 can, with the aid of the adapter 1558 and/or modem 1560, manage storage provided by the cloud storage system as it would other types of external storage. For instance, the external storage interface 1526 can be configured to provide access to cloud storage sources as if those sources were physically connected to the computer 1502.

The computer 1502 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 16:
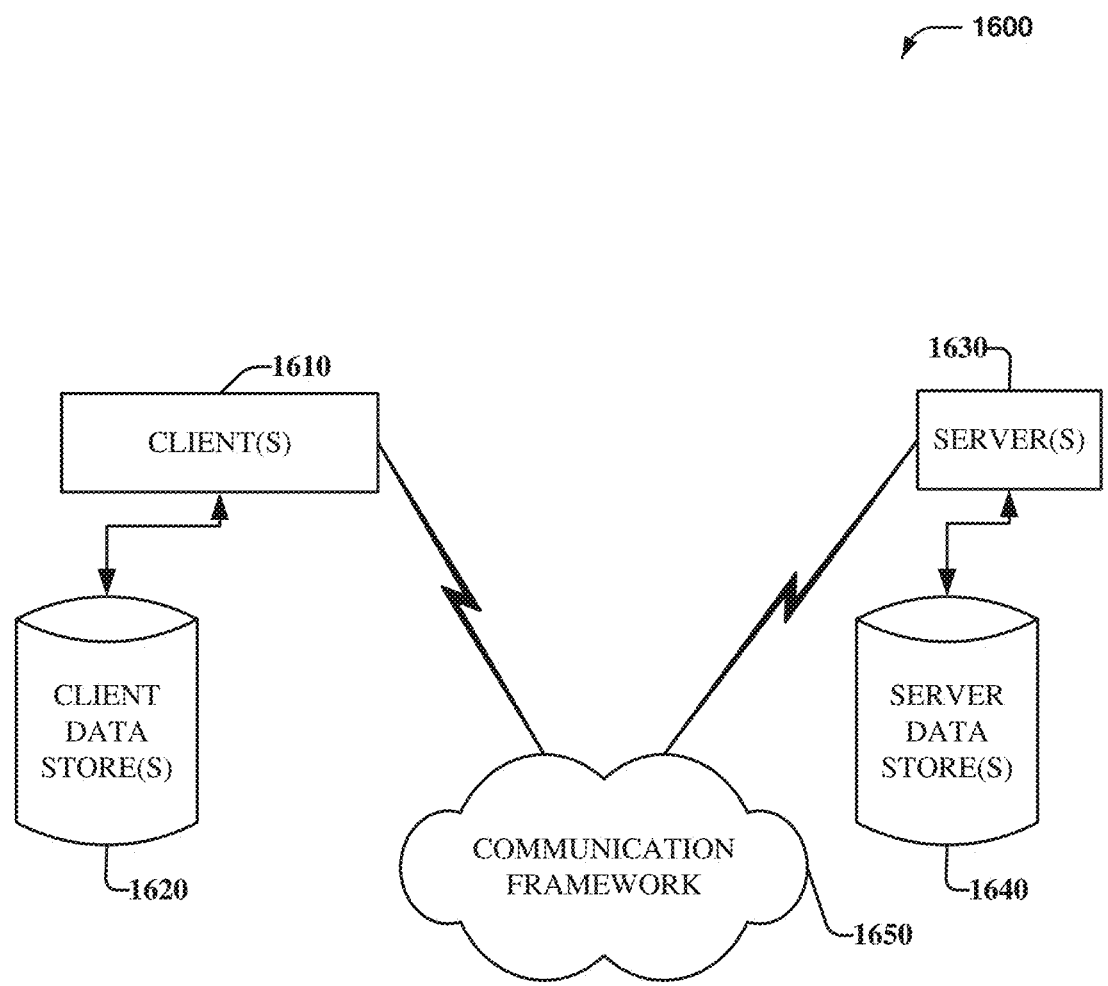
FIG. 16 illustrates an example networking environment operable to execute various implementations described herein.

FIG. 16 is a schematic block diagram of a sample computing environment 1600 with which the disclosed subject matter can interact. The sample computing environment 1600 includes one or more client(s) 1610. The client(s) 1610 can be hardware and/or software (e.g., threads, processes, computing devices). The sample computing environment 1600 also includes one or more server(s) 1630. The server(s) 1630 can also be hardware and/or software (e.g., threads, processes, computing devices). The servers 1630 can house threads to perform transformations by employing one or more embodiments as described herein, for example. One possible communication between a client 1610 and a server 1630 can be in the form of a data packet adapted to be transmitted between two or more computer processes. The sample computing environment 1600 includes a communication framework 1650 that can be employed to facilitate communications between the client(s) 1610 and the server(s) 1630. The client(s) 1610 are operably connected to one or more client data store(s) 1620 that can be employed to store information local to the client(s) 1610. Similarly, the server(s) 1630 are operably connected to one or more server data store(s) 1640 that can be employed to store information local to the servers 1630.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject claimed innovation are provided in the subject matter that follows:

1. A system, comprising: a processor that executes computer-executable components stored in a memory, the computer-executable components comprising: a magnification component that magnifies a portion of a medical image; a recognition component that recognizes an anatomical structure depicted in the portion of the medical image; and a recommendation component that recommends one or more sets of computing algorithms or computing operations based on the recognized anatomical structure.

2. The system of any preceding clause, wherein the computer-executable components further comprise: a menu component that displays the one or more recommended sets of computing algorithms or computing operations in a drop-down menu.

3. The system of any preceding clause, wherein the drop-down menu lists the one or more recommended sets of computing algorithms or computing operations in order of specificity.

4. The system of any preceding clause, wherein the computer-executable components further comprise: an execution component that executes a computing algorithm or computing operation selected from the one or more recommended sets of computing algorithms or computing operations, wherein the selected computing algorithm or computing operation computationally operates on the portion of the medical image and computationally ignores a remainder of the medical image.

5. The system of any preceding clause, wherein the recognition component recognizes the anatomical structure by employing image recognition.

6. The system of any preceding clause, wherein the recognition component recognizes the anatomical structure based on metadata corresponding to the medical image.

7. The system of any preceding clause, wherein the recommendation component recommends the one or more sets of computing algorithms or computing operations by employing an ontology that maps anatomical structures to computing algorithms or computing operations.

8. A computer-implemented method, comprising: magnifying, by a device operatively coupled to a processor, a portion of a medical image; recognizing, by the device, an anatomical structure depicted in the portion of the medical image; and recommending, by the device, one or more sets of computing algorithms or computing operations based on the recognized anatomical structure.

9. The computer-implemented method of any preceding clause, further comprising: displaying, by the device, the one or more recommended sets of computing algorithms or computing operations in a drop-down menu.

10. The computer-implemented method of any preceding clause, wherein the drop-down menu lists the one or more recommended sets of computing algorithms or computing operations in order of specificity.

11. The computer-implemented method of any preceding clause, further comprising: executing, by the device, a computing algorithm or computing operation selected from the one or more recommended sets of computing algorithms or computing operations, wherein the selected computing algorithm or computing operation computationally operates on the portion of the medical image and computationally ignores a remainder of the medical image.

12. The computer-implemented method of any preceding clause, wherein the recognizing the anatomical structure employs image recognition.

13. The computer-implemented method of any preceding clause, wherein the recognizing the anatomical structure is based on metadata corresponding to the medical image.

14. The computer-implemented method of any preceding clause, wherein the recommending the one or more sets of computing algorithms or computing operations employs an ontology that maps anatomical structures to related computing algorithms or computing operations.

15. A computer program product for facilitating an augmented inspector interface with targeted, context-driven algorithms, the computer program product comprising a computer readable memory having program instructions embodied therewith, the program instructions executable by a processing component to cause the processing component to: magnify a portion of a medical image; recognize an anatomical structure depicted in the portion of the medical image; and recommend one or more sets of computing algorithms or computing operations based on the recognized anatomical structure.

16. The computer program product of any preceding clause, wherein the program instructions are further executable to cause the processor to: display the one or more recommended sets of computing algorithms or computing operations in a drop-down menu.

17. The computer program product of any preceding clause, wherein the drop-down menu lists the one or more recommended sets of computing algorithms or computing operations in order of specificity.

18. The computer program product of any preceding clause, wherein the program instructions are further executable to cause the processor to: execute a computing algorithm or computing operation selected from the one or more recommended sets of computing algorithms or computing operations, wherein the selected computing algorithm or computing operation computationally operates on the portion of the medical image and computationally ignores a remainder of the medical image.

19. The computer program product of any preceding clause, wherein the processor recognizes the anatomical structure by employing image recognition.

20. The computer program product of any preceding clause, wherein the processor recognizes the anatomical structure based on metadata corresponding to the medical image.

What is claimed is:
1. A system, comprising:
a processor; and
a memory that stores executable instructions that, when executed by the processor, facilitate performance of operations, comprising:
magnifying a portion of a medical image;
recognizing an anatomical structure depicted in the portion of the medical image;
recommending one or more sets of computing algorithms or computing operations based on the recognized anatomical structure, wherein the one or more sets of computing algorithms or computing operations comprise a feature tracking algorithm; and
rendering an animation of the anatomical structure, wherein the animation comprises one or more prior medical images, from prior to the medical image, that depict one or more prior instances of the anatomical structure.

2. The system of claim 1, wherein the operations further comprise:
displaying the one or more recommended sets of computing algorithms or computing operations in a drop-down menu.

3. The system of claim 2, wherein the drop-down menu lists the one or more recommended sets of computing algorithms or computing operations in order of specificity.

4. The system of claim 1, wherein the operations further comprise:
executing a computing algorithm or computing operation selected from the one or more recommended sets of computing algorithms or computing operations, wherein the selected computing algorithm or computing operation computationally operates on the portion of the medical image and computationally ignores a remainder of the medical image.

5. The system of claim 1, wherein the operations further comprise:
recognizing the anatomical structure by employing image recognition.

6. The system of claim 1, wherein the operations further comprise:
recognizing the anatomical structure based on metadata corresponding to the medical image.

7. The system of claim 1, wherein the operations further comprise:
recommending the one or more sets of computing algorithms or computing operations by employing an ontology that maps anatomical structures to computing algorithms or computing operations.

8. The system of claim 1, wherein the one or more sets of computing algorithms or computing operations further comprise a diagnostic algorithm.

9. The system of claim 1, wherein the one or more sets of computing algorithms or computing operations further comprise a prognostic algorithm.

10. A computer-implemented method, comprising:
magnifying, by a device operatively coupled to a processor, a portion of a medical image;
recognizing, by the device, an anatomical structure depicted in the portion of the medical image;
recommending, by the device, one or more sets of computing algorithms or computing operations based on the recognized anatomical structure, wherein the one or more sets of computing algorithms or computing operations comprise a feature tracking algorithm; and
rendering, by the device, an animation of the anatomical structure, wherein the animation comprises one or more prior medical images, from prior to the medical image, that depict one or more prior instances of the anatomical structure.

11. The computer-implemented method of claim 10, further comprising:

displaying, by the device, the one or more recommended sets of computing algorithms or computing operations in a drop-down menu.

12. The computer-implemented method of claim 11, wherein the drop-down menu lists the one or more recommended sets of computing algorithms or computing operations in order of specificity.

13. The computer-implemented method of claim 10, further comprising:
executing, by the device, a computing algorithm or computing operation selected from the one or more recommended sets of computing algorithms or computing operations, wherein the selected computing algorithm or computing operation computationally operates on the portion of the medical image and computationally ignores a remainder of the medical image.

14. The computer-implemented method of claim 10, wherein the recognizing the anatomical structure employs image recognition.

15. The computer-implemented method of claim 10, wherein the recognizing the anatomical structure is based on metadata corresponding to the medical image.

16. The computer-implemented method of claim 10, wherein the recommending the one or more sets of computing algorithms or computing operations employs an ontology that maps anatomical structures to related computing algorithms or computing operations.

17. A computer program product for facilitating an augmented inspector interface with targeted, context-driven algorithms, the computer program product comprising a computer readable memory having program instructions embodied therewith, the program instructions executable by a processor to cause the processor to:
magnify a portion of a medical image;
recognize an anatomical structure depicted in the portion of the medical image;
recommend one or more sets of computing algorithms or computing operations based on the recognized anatomical structure, wherein the one or more sets of computing algorithms or computing operations comprise a feature tracking algorithm; and
render an animation of the anatomical structure, wherein the animation comprises one or more prior medical images, from prior to the medical image, that depict one or more prior instances of the anatomical structure.

18. The computer program product of claim 17, wherein the program instructions are further executable to cause the processor to:
display the one or more recommended sets of computing algorithms or computing operations in a drop-down menu.

19. The computer program product of claim 18, wherein the drop-down menu lists the one or more recommended sets of computing algorithms or computing operations in order of specificity.

20. The computer program product of claim 17, wherein the program instructions are further executable to cause the processor to:
execute a computing algorithm or computing operation selected from the one or more recommended sets of computing algorithms or computing operations, wherein the selected computing algorithm or computing operation computationally operates on the portion of the medical image and computationally ignores a remainder of the medical image.

* * * * *